(12) United States Patent
Wanebo et al.

(10) Patent No.: US 7,820,718 B1
(45) Date of Patent: Oct. 26, 2010

(54) COMBINATIONS OF CERAMIDE AND CHEMOTHERAPEUTIC AGENTS FOR INDUCING CELL DEATH AND USES THEREOF IN TREATING CANCER

(75) Inventors: Harold J. Wanebo, East Greenwich, RI (US); Shashikant Mehta, Warwick, RI (US)

(73) Assignee: Roger Williams Hospital, Providence, RI (US)

( * ) Notice: Subject to any disclaimer, the term of this patent is extended or adjusted under 35 U.S.C. 154(b) by 0 days.

(21) Appl. No.: 09/287,884

(22) Filed: Apr. 7, 1999

(51) Int. Cl.
*A61K 31/16* (2006.01)

(52) U.S. Cl. .................................. 514/629; 514/449

(58) Field of Classification Search ............... 514/449, 514/669, 629
See application file for complete search history.

(56) References Cited

U.S. PATENT DOCUMENTS

| | | | |
|---|---|---|---|
| 5,478,860 A | | 12/1995 | Wheeler |
| 5,631,394 A | * | 5/1997 | Wei et al. ............... 556/404 |
| 6,465,448 B1 | * | 10/2002 | Gerson et al. ............ 514/183 |
| 6,664,288 B1 | * | 12/2003 | Pardee et al. ............ 514/449 |
| 6,841,537 B1 | * | 1/2005 | Joshi et al. ............... 514/44 |

FOREIGN PATENT DOCUMENTS

WO WO94/04541 * 3/1994

OTHER PUBLICATIONS

Mycek, et al. "Lippincott's Illustrated Reviews: Pharmacology, 2nd ed." 1997, Lippincott-Raven Pub. p. 376, 391-392.*
Hartfield PJ et al. "Ceramide induces apoptosis in PC12 cells," 1997 FEBS Letters vol. 401, pp. 148-152.*
Cai Z et al., "Alteration of the sphingomyelin/ceramide pathway is associated with resistance of human breast carcinoma . . . ," 1997 J Biological Chemistry 272(11): 6918-6926.*
Spencer CM and Faulds D, "Paclitaxel. A review of its pharmacodynamis and pharmacokinetic properties and therapeutic potential in the treatment of cancer," 1994 Drugs 48(5): 794-847.*
Cecil Textbook of Medicine, 21st Edition (2000), Goldman & Bennett (Editors), W.B. Saunders Company (Publisher), Chapter 198, pp. 1060-1074.*
BASF, "Cremophor® EL" Technical Leaflet [online], Jul. 1997; retrieved on Nov. 3, 2005 from the internet <<http://www2.zzu.edu.cn/syzx/lijx/cremophorel.pdf >>.*
Baselga, J. et al. (1997) "HER2 overexpression and paclitaxel sensitivity in breast cancer: therapeutic implications," *Oncol.* Mar. 11 (3 suppl 2), 43-48. (Exhibit 1).

Jayadev, S. et al. (1995) "Role for ceramide in cell cycle arrest," *J. Biol. Chem.* 270(5): 2047-2052. (Exhibit 2).
Mathias, S. et al. (1998) "Signal transduction of stress via ceramide," *Biochem. J.* 335:465-480. (Exhibit 3).
Perez, E. A. et al. (1998) "Sequence-dependent cytotoxicity of etoposide and paclitaxel in human breast and lung cancer cell lines," *Cancer Chemother. Pharmacol.* 41(6): 448-452. (Exhibit 4).
Shirahama, T. et al. (1997) "In vitro and in vivo induction of apoptosis by sphingosine and N, N-dimethylsphingosin in human epidermoid carcinoma KB-3-1 and its multidrug-resistant cells," *Clin. Cancer Res.* 3:257-264. (Exhibit 5).
Ping SE. Barrett GL. "Ceramide can induce cell death in sensory neurons, whereas ceramide analogues and sphingosine promote survival", *J Neurosci Res.* vol. 54, No. 2, Oct. 15, 1998, pp. 206-213 (Exhibit B).
Myrick, D., et al., "Taxol and ceramide act synergistically in the growth inhibition of Jurkat, a leukemic T-cell line", *Faseb Journal*, vol. 11, No. 2, p. A546 (Abstract, 1997).
Myrick, D.C., et al., "Paclitaxel-induced apoptosis in Jurkat, a leukemic T-cell, is enhanced by ceramide", *FASEB Journal*, vol. 13, No. 4, Part 1, p. A191 (Abstract, Mar. 12, 1999).
Myrick, Dorkina, et al., "Paclitaxel-induced apoptosis in Jurkat, a leukemic T cell line, is enhanced by ceramide", *Leukemia Research*, vol. 23, No. 6, pp. 569-578 (Jun. 1999).

* cited by examiner

*Primary Examiner*—James D Anderson
(74) *Attorney, Agent, or Firm*—John P. White; Cooper & Dunham LLP

(57) ABSTRACT

This invention provides a method for increasing apoptosis in tumor cells and a method of decreasing a size of a tumor, said methods comprising contacting the tumor cells with: a) an effective amount of at least one antitumor chemotherapeutic agent and b) an effective amount of a ceramide, sequentially or concomitantly, wherein the apoptosis induced by the combination of the antitumor chemotherapeutic agent and the ceramide is greater than the apoptosis induced by contact of the tumor cells with either the antitumor chemotherapeutic agent alone or the ceramide alone. This invention also provides a method of treating cancer in a subject which comprises a method according to either of the above-described methods. This invention provides a method for treating cancer in a subject comprising administering to the subject an effective amount of at least one antitumor chemotherapeutic agent and an effective amount of at least one ceramide, sequentially or concomitantly. This invention provides a pharmaceutical composition comprising at least one antitumor chemotherapeutic agent in an amount effective to induce apoptosis of tumor cells and at least one ceramide in an amount effective to induce apoptosis of tumor cells and a pharmaceutically acceptable carrier.

26 Claims, 21 Drawing Sheets (24 Hours)

0.93%

0.64%

1.16%

25.49%

(48 Hours)

0.77%

0.33%

19.60%

66.05%

Control - No Additions (24 Hours)

$G_0$-$G_1$: 59.1%
S: 33.5%
$G_2$-M: 7.4%

Ceramide 25 μg/ml (24 hours)

$G_0$-$G_1$: 56.7%
S: 26.8%
$G_2$-M: 16.5%

$G_0$-$G_1$: 9.5%
S: 28.7%
$G_2$-M: 61.8%

Paclitaxel 600 ng/ml (24 hours)

$G_0$-$G_1$: 17.2%
S: 37.2%
$G_2$-M: 45.6%

Ceramide 25µg/ml (24 hours)
+ Paclitaxel 600 ng/ml $G_0$-$G_1$: 53.9%
S: 40.2%
$G_2$-M: 6.0%

Control - No additions (48 hours)

$G_0$-$G_1$: 54.9%
S: 39.6%
$G_2$-M: 5.5%

Ceramide 25 μg/ml (48 hours)

G₀-G₁: 16.7%
S: 25.2%
G₂-M: 58.2%

Paclitaxel 600 ng/ml (48 hours)

G₀-G₁: 71.6%
S: <1%
G₂-M: 28.4%

Ceramide 25µg/ml (48 hours)
+ Paclitaxel 600 ng/ml

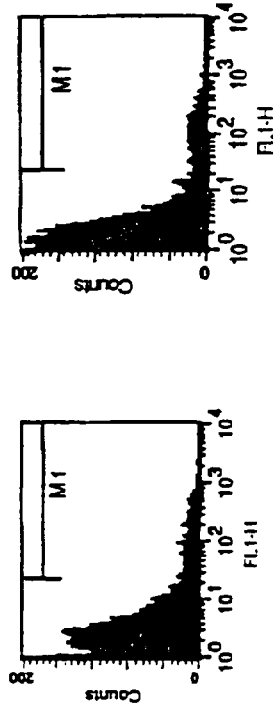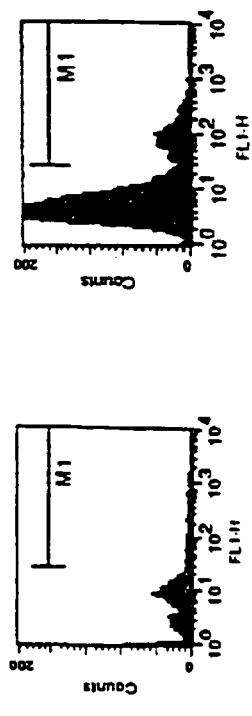

Time Kinetics Of The Induction Of Apoptosis By Paclitaxel And Ceramide Acting In Combination.

FIGURE 10A, FIGURE 10B, FIGURE 10C, FIGURE 10D — 24 Hours Of Taxol And/Or Ceramide Exposure.

FIGURE 10A: Control - no additions, Apoptosis: 8.7%
FIGURE 10B: Ceramide (25 μg/ml), Apoptosis: 9.7%
FIGURE 10C: Paclitaxel (600 ng/ml), Apoptosis: 18.35%
FIGURE 10D: Ceramide 25 μg/ml + Paclitaxel 600 ng/ml, Apoptosis: 53.7%

FIGURE 10E, FIGURE 10F, FIGURE 10G, FIGURE 10H — 48 Hours Of Taxol And/Or Ceramide Exposure.

FIGURE 10E: Control - no additions, Apoptosis: 7.8%
FIGURE 10F: Ceramide (25 μg/ml), Apoptosis: 13.6%
FIGURE 10G: Paclitaxel (600 ng/ml), Apoptosis: 54.7%
FIGURE 10H: Ceramide (25 μg/ml) + Paclitaxel 600 ng/ml, Apoptosis: 84.9%

COMBINATIONS OF CERAMIDE AND CHEMOTHERAPEUTIC AGENTS FOR INDUCING CELL DEATH AND USES THEREOF IN TREATING CANCER

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Paclitaxel, an alkaloid compound originally derived from the bark of the Pacific yew tree, is currently used in treatment of breast and ovarian as well as many other types of cancer, including non-small cell lung carcinoma, prostate, head and neck cancer, and lymphoma.(1-9) The main site of paclitaxel's action is the microtubules of eukaryotic cells, whose functions include formation of the mitotic spindle during cytokinesis, intracellular transport, shape maintenance, cell motility and attachment, and regulation of transmembrane signals from cell-surface receptors.(10) Paclitaxel acts predominantly by promoting the polymerization of tubulin subunits into microtubules and by preventing depolymerization of the microtubules once they are formed.(11) Paclitaxel has been shown to block cell growth in the $G_2$-M phase of the cell cycle, with subsequent inhibition of mitosis.(12,13) Changes in the structure of microtubules and the mitotic spindle apparatus lead not only to inhibition of cellular division and migration of chromosomes but also to chromosomal breakage.(14)

Sphingomyelin, a cell membrane component, can be hydrolyzed to ceramide and phosphorylcholine by acid or neutral sphingomyelinase.(15,16) This hydrolysis event initiates an intracellular signalling cascade associated with the stimulation of numerous biological activities, including induction of apoptosis(17-24) and arrest of cell growth in the $G_0$-$G_1$ phase.(25-27)

The rationale for combination of paclitaxel and ceramide is based on previous studies that demonstrated activation of Fas expression on leukemic cells by another chemotherapeutic agent, vincristine, which acts primarily by destroying the mitotic spindle in the $G_2$-M phase.(28-30) Since ceramide has been reported to mediate, in part, Fas activation,(15,22,23) two agents that appear to converge on some common point in the sphingomyelin/ceramide pathway was evaluated.

Moreover, since these agents act in different phases of the cell cycle, and not all tumor cells can be arrested and/or eliminated in the $G_2$-M phase by paclitaxel exposure, additional anti-cancer agents may be needed in the therapeutic regimen. This is supported by the observation that paclitaxel combined with other chemotherapeutic agents in treatment of a variety of cancers, including leukemia, typically produces a stronger tumor cell growth inhibition than a single chemotherapeutic agent.(31-33) Therefore the experiments combine ceramide, a reported $G_0$-$G_1$ blocker, with paclitaxel to prevent proliferation of cells that escape the $G_2$-M arrest induced by paclitaxel.

This invention provides a method of combination therapy wherein paclitaxel (or other chemotherapeutic agents) and ceramide interact synergistically to induce cytotoxicity and apoptosis in carcinoma cells thereby decreasing the growth of cancer cells.

SUMMARY OF THE INVENTION

This invention provides a method for increasing apoptosis in tumor cells comprising contacting the tumor cells with: a) an effective amount of at least one antitumor chemotherapeutic agent and b) an effective amount of a ceramide, sequentially or concomitantly, wherein the apoptosis induced by the combination of the antitumor chemotherapeutic agent and the ceramide is greater than the apoptosis induced by contact of the tumor cells with either the antitumor chemotherapeutic agent alone or the ceramide alone, thereby increasing apoptosis in tumor cells.

This invention also provides a method of decreasing a size of a tumor comprising contacting the tumor with: a) an effective amount of at least one antitumor chemotherapeutic agent and b) an effective amount of a ceramide, sequentially or concomitantly, wherein the induced decrease in size of the tumor is greater than the decrease in size of a tumor after contacting the tumor with either the antitumor chemotherapeutic agent alone or the ceramide alone, thereby decreasing the size of the tumor.

This invention further provides a method of treating cancer in a subject which comprises the method according to either of the above-described methods of increasing apoptosis in tumor cells or the above-described of method decreasing a size of a tumor in the subject.

This invention provides a pharmaceutical composition comprising at least one antitumor chemotherapeutic agent in an amount effective to induce apoptosis of tumor cells and at least one ceramide in an amount effective to induce apoptosis of tumor cells and a pharmaceutically acceptable carrier.

This invention provides a method for treating cancer in a subject comprising administering to the subject an effective amount of at least one antitumor chemotherapeutic agent and an effective amount of at least one ceramide, sequentially or concomitantly.

BRIEF DESCRIPTION OF THE FIGURES

(FIG. 3A) Untreated Jurkat control cells with no additions of paclitaxel or ceramide; (FIG. 3B) with addition of 25 µg/ml of ceramide; (FIG. 3C) with 0.6 ng/ml of paclitaxel; (FIG. 3D) with 0.6 ng/ml of paclitaxel and 25 µg/ml of ceramide combined; (FIG. 3E) with 6.0 ng/ml of paclitaxel; and (FIG. 3F) with 6.0 ng/ml of paclitaxel and 25 µg/ml ceramide combined.

(FIG. 4A) Untreated Jurkat control cells with no additions of paclitaxel or ceramide; (FIG. 4B) with 25 µg/ml of ceramide; (FIG. 4C) with 0.6 ng/ml of paclitaxel; (FIG. 4D) with 6.0 ng/ml of paclitaxel; (FIG. 4E) with 0.6 ng/ml of paclitaxel and 25 µg/ml of ceramide combined; and (FIG. 4F) with 6.0 ng/ml of paclitaxel and 25 µg/ml of ceramide combined.

FIGS. 5A and 5E represent untreated control cells; FIGS. 5B and 5F represent cells treated with 25 µg/ml ceramide; FIGS. 5C and 5G represent cells treated with 0.6 ng/ml paclitaxel; and FIGS. 5D and 5H represent cells treated with both ceramide and paclitaxel. The percentage of apoptotic cells obtained by flow cytometric analysis is shown below each figure.

FIG. 6A) and ceramide (0-50 µg/ml; FIG. 6B) and the y-axis represents optical density (540 nm) of live cells that incorporated MTT dye. Each data point represents an average and a standard deviation of triplicate determinations.

FIG. 10. TUNEL Assay for the Measurements of Paclitaxel (Taxol) and Ceramide Induced Apoptosis of Tu138 cells. For the measurement of apoptosis, Tu138 cells were cultured with or without paclitaxel (Taxol) (600 ng/ml) and/or ceramide (25 µg/ml) as described FIGS. 9A-9H. The analyses of acquired samples were based on an antibody binding to DNA fragments shown as fluorescence on x-axis and cell count of y-axis. For the positive control, Tu138 cells were treated with DNAase for 10 minutes at room temperature prior to the acquisition on FACScan. The percent shown underneath each scan was obtained by the use of CELL Quest software (Becton Dickinson, Calif.) and is represented by M1.

DETAILED DESCRIPTION OF THE INVENTION

Figure 1:
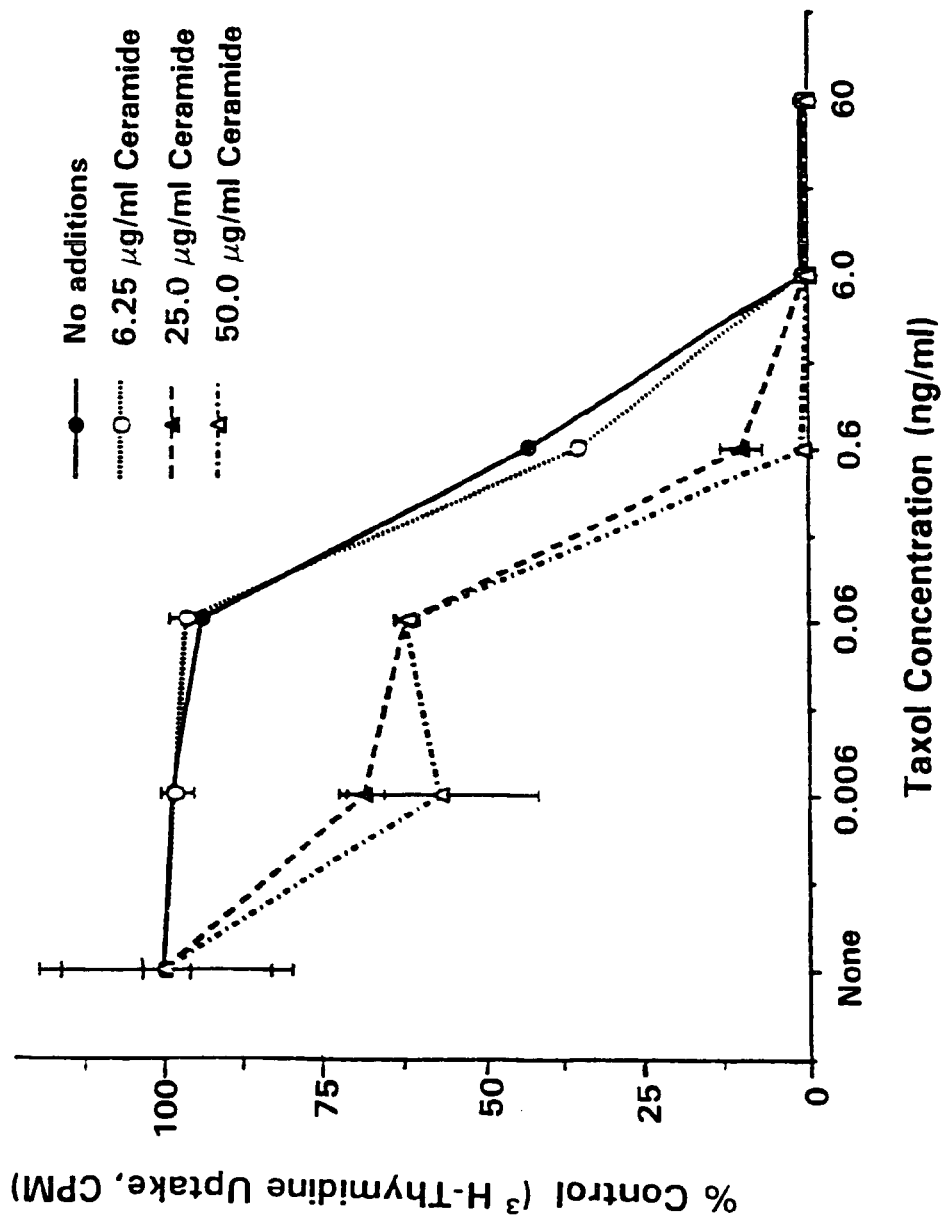
FIG. 1. Effect of paclitaxel (taxol) and ceramide on Jurkat cell growth inhibition. Jurkat cells were maintained as described in Materials and Methods, resuspended at a density of $1 \times 10^6$ cells/ml, washed by centrifugation for 5 minutes at 1500 rpm, and plated in a final volume of 0.2 ml per well in complete RPMI 1640 medium containing 0% to 10% fetal bovine serum. Paclitaxel (0 to 60 ng/ml and ceramide (0 to 50 µg/ml) were added to Jurkat cells either alone or in combination, and proliferation was measured in cpm using a 3-day $^3$H thymidine uptake assay. The data are normalized to respective cell control.

This invention provides a method for increasing apoptosis in tumor cells comprising contacting the tumor cells with: a) an effective amount of at least one antitumor chemotherapeutic agent and b) an effective amount of a ceramide, sequentially or concomitantly, wherein the apoptosis induced by the combination of the antitumor chemotherapeutic agent and the ceramide is greater than the apoptosis induced by contact of the tumor cells with either the antitumor chemotherapeutic agent alone or the ceramide alone, thereby increasing apoptosis in tumor cells.

As used herein "increasing apoptosis" is defined as an increase in the rate of programmed cell death, i.e. more cells are induced into the death process as compared to exposure (contact with) either the chemotherapeutic agent alone or the ceramide alone. Increasing apoptosis also includes the inhibition of cell division which results in a decrease in the total number of viable tumor cells.

As used herein "contacting tumor cells" is defined as exposing the tumor cells to combination therapy, i.e. administering to the tumor cells directly or indirectly, chemotherapeutic agent(s) and ceramide by local, regional or syatemic means.

As used herein a "ceramide" is any N-acylsphingosine. Ceramides include sphingolipids in which the sphingosine is acylated with a fatty acid acyl CoA derivative to form an N-acylsphingosine. Ceramide may be either naturally occurring or chemically synthesized. Preferably, the carbon chain length is less than 18 carbons. Examples include C6-ceramide (N-hexanoyl-D-sphingosine), C2-ceramide (N-acetyl-D-sphingosine), C8-ceramide (N-octyl-D-sphingosine) and C16-ceramide (N-palmitoyl-D-sphingosine. Other ceramides are known to one of skill in the art.

Preferably, the ceramide (which is lipid soluble) is water soluble or made water soluble to enable contact with the tumor cells in a subject. Ceramide (6%) may be solubilized initially in alcohol and then subsequently diluted in saline or a cremophore.

This invention also provides a method of decreasing a size of a tumor comprising contacting the tumor with: a) an effective amount of at least one antitumor chemotherapeutic agent and b) an effective amount of a ceramide, sequentially or concomitantly, wherein the induced decrease in size of the tumor is greater than the decrease in size of a tumor after contacting the tumor with either the antitumor chemotherapeutic agent alone or the ceramide alone, thereby decreasing the size of the tumor.

As used herein "decreasing the size of a tumor" is defined as a reduction in the size of a tumor; the reduction is accomplished by reducing the number of proliferating tumor cells in the tumor, i.e. reducing cell division of the tumor cells, and by inducing cytotoxicity or cell death (apoptosis) of existing tumor cells. Accordingly, tumor growth is arrested or prevented.

In an embodiment of either the above-described method of increasing apoptosis in tumor cells or the above-described of method decreasing a size of a tumor via combination therapy with a chemotherapeutic agent (e.g. paclitaxel) and ceramide, the tumor cells may be or the tumor is composed of cancer cells selected from the group consisting of, but not limited to, leukemic cells, prostate cancer cells, pancreatic cancer cells and squamous cell carcinoma cells, breast carcinoma cells, melanoma cells, basal cell carcinoma cells, neuroblastoma cells, glioblastoma multiforme cells, myeloid leukemic cells, colon carcinoma cells, endometrial carcinoma cells, lung carcinoma cells, ovarian carcinoma cells, cervical carcinoma cells, osteosarcoma cells and lymphoma cells. In further embodiments of the above-described methods, the ceramide may be a C2-ceramide, C6-ceramide, C8-ceramide, C16-ceramide, or a higher order of ceramides.

In another embodiment of either the above-described method of increasing apoptosis in tumor cells or the above-described of method decreasing a size of a tumor, the tumor cells are or the tumor is contacted first with at least one antitumor chemotherapeutic agent (e.g. paclitaxel) and subsequently contacted with the ceramide.

This invention further provides a method of treating cancer in a subject which comprises the method according to either of the above-described methods of increasing apoptosis in tumor cells or the above-described of method decreasing a size of a tumor in the subject, wherein the tumor cells or the tumor are present in the subject.

In an embodiment of the method of treating cancer in a subject according to any of the above-described methods, wherein the ceramide may be a C2-ceramide, C6-ceramide, C8-ceramide, C16-ceramide or a higher order of ceramide. In further embodiments more than one ceramide may be administered to the subject.

In another embodiment of either the above-described method of increasing apoptosis in tumor cells or the above-described of method decreasing a size of a tumor via combination therapy with a chemotherapeutic agent (e.g. paclitaxel) and ceramide, the antitumor chemotherapeutic agent is paclitaxel or compounds structurally related to the paclitaxel family of compounds, e.g. alkaloids. The antitumor chemotherapeutic agent in any of the above-described methods may also include but not be limited to chemotherapeutic agents such as doxorubicin, cis-platin, cyclophosphamide, etoposide, vinorelbine, vinblastin, tamoxifen, colchinin, 2-methoxyestradiol. In further embodiments of the above-described methods the paclitaxel may be used together with another antitumor chemotherapeutic; combinations of any of the above-listed antitumor chemotherapeutic agents may be used.

In still further embodiments of either the above-described method of increasing apoptosis in tumor cells or the above-described of method decreasing a size of a tumor via combination therapy with a chemotherapeutic agent (e.g. paclitaxel) and ceramide, the contacting with the antitumor chemotherapeutic agent (exposure of the tumor cells to the antitumor chemotherapeutic agent) is effected by cremophore delivery or by liposome-mediated delivery and the contacting with (exposure to) the ceramide is effected by alcohol-mediated delivery or liposome-mediated delivery.

As used herein a "cremophore" is a solvent that permits solubilization of a drug or compound. Various cremophores are well known to one of skill in the art, including but not limited to oil based solvents.

In still further embodiments of any of the above-described methods of combination therapy, the route of administration (contacting the tumor cells) effected by cremophore-mediated delivery, alcohol-mediated delivery or liposome-mediated delivery of the ceramide(s) or of the antitumor chemotherapeutic agent(s) may be selected from but not limited to any of the following routes of administration: intravenous, intraperitoneal, intra-thecal, intralymphatical, intramuscular, intralesional, parenteral, epidural, or subcutaneous administration; by infusion, by aerosol delivery; or by topical, oral, nasal, anal, ocular or otic delivery.

This invention also provides a pharmaceutical composition comprising at least one antitumor chemotherapeutic agent in an amount effective to induce apoptosis of tumor cells and at least one ceramide in an amount effective to induce apoptosis of tumor cells and a pharmaceutically acceptable carrier.

This invention provides a method for treating cancer in a subject comprising administering to the subject an effective amount of at least one antitumor chemotherapeutic agent and an effective amount of at least one ceramide, sequentially or concomitantly.

As used herein an "effective amount" is defined as an amount of antitumor chemotherapeutic agent and the ceramide which provides the maximum apoptosis of tumor cells at the least toxicity to nontumor cells. The effective amount may be measured as the concentration of antitumor chemotherapeutic agent and ceramide which induces a 50% death rate (ED 50) of tumor cells.

In an embodiment of the above-described method for treating cancer in a subject, at least one antitumor chemotherapeutic agent and subsequently at least one ceramide is administered to the subject.

In another embodiment of the above-described method for treating cancer in a subject, at least one ceramide and subsequently at least one antitumor chemotherapeutic agent is administered to the subject.

In a further embodiment of the above-described method for treating cancer in a subject, the antitumor chemotherapeutic agent is paclitaxel and the ceramide is C6-ceramide. In other embodiments the antitumor chemotherapeutic agent is a compounds structurally related to the paclitaxel family of compounds, e.g. alkaloids. The antitumor chemotherapeutic agent in any of the above-described methods may also include but not be limited to chemotherapeutic agents such as doxorubicin, cis-platin, cyclophosphamide, etoposide, vinorelbine, vinblastin, tamoxifen, colchinin, 2-methoxyestradiol. In further embodiments of the above-described methods the paclitaxel may be used together with another antitumor chemotherapeutic; combinations of any of the above-listed antitumor chemotherapeutic agents may be used. In still further embodiments of the above-described methods the ceramide may be a C2-ceramide, C8-ceramide or a higher order of ceramide. In additional embodiments more than one ceramide may be administered to the subject.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Methods and Materials

1st Series of Experiments

Paclitaxel-induced Apoptosis in Jurkat, a Leukemic T Cell Line, is Enhanced by Ceramide It is hypothesized that the lipid second messenger, ceramide, and microtubule-directed chemotherapeutic agents might engage converging pathways in inducing apoptosis. The studies described herein demonstrate that simultaneous treatment of Jurkat cells with paclitaxel and ceramide enhanced paclitaxel-induced cell growth inhibition. Cell-cycle analysis indicated a significant increase in the hypodiploid population over that observed with paclitaxel treatment alone. Morphologic evaluation and a TUNEL assay confirmed a dramatic increase in apoptosis in Jurkat cells treated with the combination of these two agents. This is the first demonstration that paclitaxel and ceramide interact in a supra-additive manner to decrease leukemic T-cell growth, suggesting a possible application of paclitaxel and ceramide in combination therapy.

Materials and Methods

Cell Proliferation Assays. Jurkat, a human acute T cell leukemia line (American Type Culture Collection, Rockville, Md.) was routinely maintained in an incubator at 37° C. and 5% $CO_2$ at a density of $0.5 \times 10^6$ cells/ml in complete RPMI 1640 medium containing 1% L-glutamine, 1% penicillin-streptomycin (GIBCO Biological Research Laboratories, Grand Island, N.Y.) and 10%-20% fetal bovine serum (Atlanta Biologicals, Atlanta, Ga.). For proliferation assays, cells were washed twice and resuspended in complete RPMI 1640 medium at a density of $0.5 \times 10^6$ cells/ml in a final volume of 0.2 ml per well in a 96-well microtiter plate. Paclitaxel (Bristol-Myers Squibb Co., Princeton, N.J.) and ceramide were added as indicated below. DNA synthesis was assessed by the addition of $^3$H-thymidine (1 μCi/well; specific activity ~6.7 $C_i$/mmol; ICN Pharmaceuticals, Costa Mesa, Calif.) uptake 24 hours before the end of the 72 hour growth period at a final concentration of 1 μCi/well. Cells were harvested on glass microfibre filters (Whatman Co., Maidstone, England) with a cell harvester (Cambridge Technology, Cambridge, Mass.) and counted on a LKB Wallac 1214 RackBeta 'Excel' Beta spectrophotometer (Wallac Oy, Turku, Finland) after the addition of an 0.5-ml EcoLite (ICN Pharmaceuticals, Costa Mesa, Calif.) scintillation cocktail.

Paclitaxel and Ceramide Treatment of Cell Cultures. Paclitaxel was added to Jurkat cell cultures at final concentrations ranging from 0.006 to 6000 ng/ml. Exogenous ceramide ($C_6$—N-hexanoyl-D-sphingosine; Sigma Chemicals, St. Louis, Mo.) was dissolved in 100% ethanol, and, after dilution with culture medium, was added to cell cultures at final concentrations ranging from 5 to 25 μg/ml. An equal proportion of 100% ethanol was diluted in complete RPMI 1640 medium and added to cell cultures in the absence of ceramide to eliminate the possibilty of alcohol cytotoxicity. To examine the effects of combination treatment, paclitaxel (0.6 ng/ml and 6.0 ng/ml) and ceramide (25 μg/ml) were added simultaneously at the beginning of cell culture.

Cell Cycle Analysis. Cells were cultured in 6-well plates (Falcon Products, St. Louis, Mo.) at a density of $0.5 \times 10^6$ cells/ml and incubated in parallel experiments with paclitaxel alone at 0.6 ng/ml and 6.0 ng/ml, ceramide alone at 25 μg/ml, and paclitaxel and ceramide in combination at 0.6 ng/ml and 6.0 ng/ml and 25 μg/ml respectively. A 3 ml aliquot was obtained from each 6-well plate at the indicated times. Cells were centrifuged twice at 1500 rpm for 5 minutes and resuspended in saline, labeled with 0.5 ml of propidium iodide (0.05 mg/ml), and analyzed by FACScan (Becton Dickinson Immunocytometry Systems, San Jose, Calif.) using ModFit LT software for cell-cycle analysis essentially as described by Look et al.(34) Cell growth was calculated as a percentage of the total population of both live and hypodiploid cells. Pie graphs (FIGS. 3A-F) were generated and normalized to a control value of 100%.

Histologic Evaluation. Cytospins (Shandon Incorporated, Pittsburgh, Pa.) of Jurkat cells treated with 0.6 ng/ml and 6.0 ng/ml paclitaxel and/or 25 μg/ml of ceramide were generated by centrifuging the cells onto glass slides (200-ml aliquot/slide) for 3 minutes at 750 rpm. Wright's stains of all slides were performed using an automated Hemastainer (Geometric Data, Wayne, Pa.). Slides were analyzed microscopically, photographed (Olympus BH 2, Tokyo, Japan) at 100, 200, and 400 power, and evaluated for morphological changes.

Terminal deoxynucleotide transferase (TdT) mediated deoxyuridine triphosphate (dUTP) nick-end labeling (TUNEL) assay. Jurkat cells were cultured in 6-well plates at a density of $0.5 \times 10^6$/ml in a total volume of 5 ml, in RPMI complete medium containing 10% fetal bovine serum at 37° C.; the cells were treated with and without 0.6 ng/ml of paclitaxel, 12.5 and 25 μg/ml of ceramide, or a combination of the two. At 24 and 48 hours, DNA strand breaks were labeled with TUNEL assay (In Situ Cell Death Detection Kit, Fluorescein; Boehringer Mannheim, Indianapolis, Ind.), and cellular apoptosis was measured by flow cytometry.

Results

Initial experiments focused on the effects of varying concentrations of ceramide on paclitaxel-mediated inhibition of Jurkat cell growth, as measured by $^3$H-thymidine uptake assay. Jurkat cells were plated in the presence of different amounts (0 to 50 μg/ml) of $C_6$-ceramide and/or paclitaxel (0 to 60 ng/ml) in RPMI-1640 culture medium containing 10% fetal bovine serum. As indicated in FIG. 1, paclitaxel at concentrations higher than 0.06 ng/ml effectively blocked thymidine incorporation of Jurkat cells. The calculated $ED_{50}$ for paclitaxel alone (n=5) was approximately 0.5 ng/ml in a 3-day exposure assay. Ceramide addition produced a marked enhancement of paclitaxel-mediated growth inhibition at 0.6 ng/ml, increasing from 56.5% to 90.1% and >99% (with 25 and 50 μg/ml of ceramide, respectively). Ceramide added alone did not cause significant Jurkat cell growth inhibition (≦6%) at all test concentrations (FIG. 1, Table 1).

TABLE 1

Taxol and ceramide-induced growth inhibition[a]

| Additions | Experiment 1 | Experiment 2 | Experiment 3 | Experiment 4 | Experiment 5 |
|---|---|---|---|---|---|
| None | 382839 ± 23416 | 444400 ± 17569 | 258826 ± 39243 | 301150 ± 25159 | 242529 ± 38947 |
| Ceramide 25 µg/ml | 378245 ± 28689 | 415740 ± 6168 | 301993 ± 67599 | 259230 ± 54914 | 189052 ± 3534 |
| Taxol 0.6 ng/ml | 52675 ± 7478 | 95563 ± 6427 | 22771 ± 5113 | 89621 ± 17579 | 98694 ± 32045 |
| Taxol 0.6 ng/ml and Ceramide 25 µg/ml | 24149 ± 2688 | 48356 ± 2777 | 1652 ± 21 | 70929 ± 16035 | 449 ± 143 |
| Taxol 6.0 ng/ml | 16592 ± 782 | 33443 ± 17976 | 13400 ± 849 | 35466 ± 7576 | 10295 ± 353 |
| Taxol 6.0 ng/ml and Ceramide 25 µg/ml | 11509 ± 965 | 8536 ± 608 | 1262 ± 288 | 8907 ± 2484 | 249 ± 147 |

[a]This table demonstrates that ceramide consistently enhances taxol mediated cell growth inhibition over a series of several experiments. The numbers displayed are actual [$^3$H]thymidine uptake counts ± SD (cpm), obtained from triplicate determination. A paired student t test demonstrated statistical significance within a 95% confidence interval.

Figure 2:
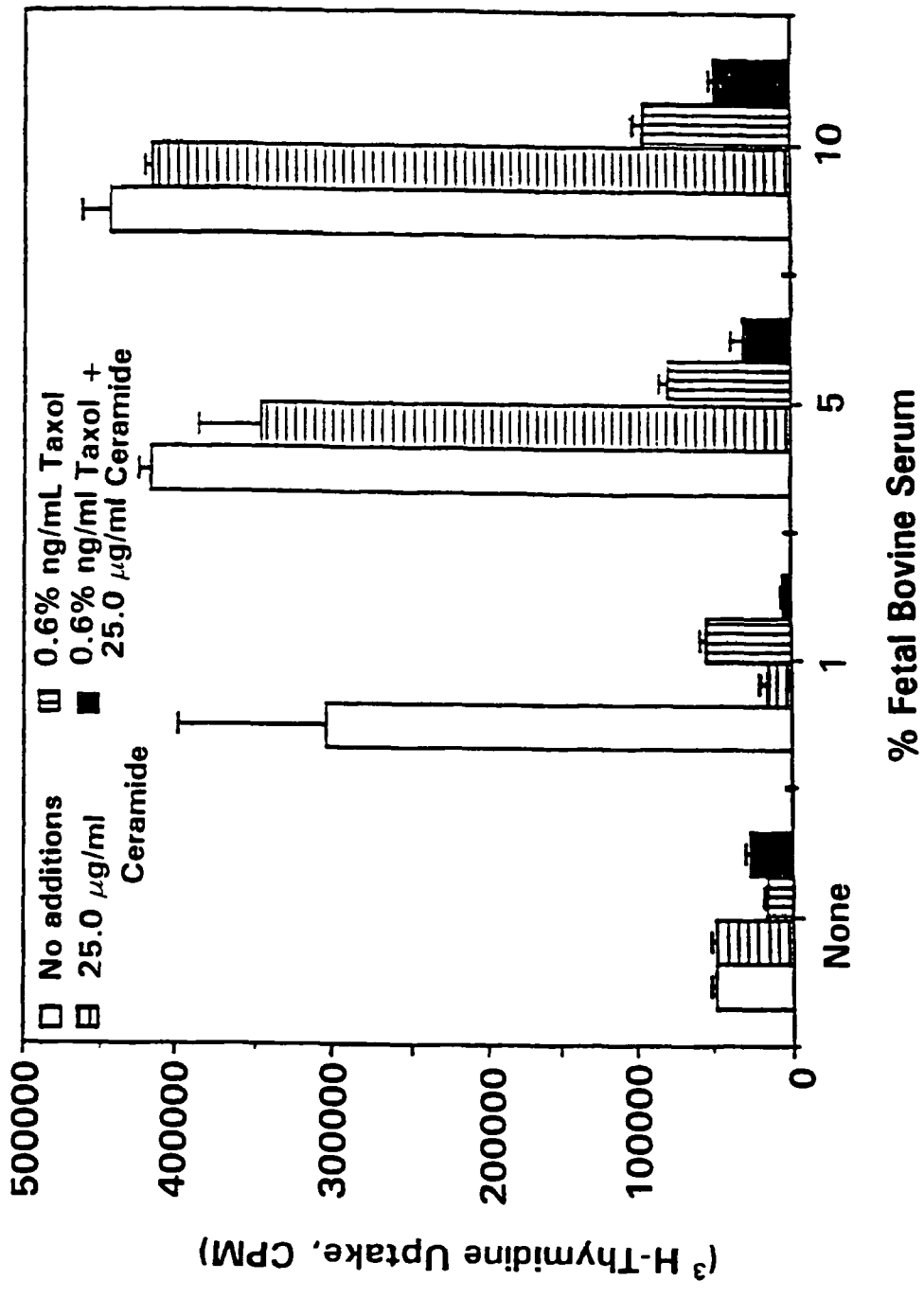
FIG. 2. Effects of Serum on Paclitaxel and Ceramide Induced Jurkat Cell Growth Inhibition. The combined effect of the addition of paclitaxel (0.6 ng/ml) and ceramide (25 µg/ml) on Jurkat cell growth in 0% to 10% fetal bovine serum is shown. Jurkat cells were maintained and treated as described in Materials and Methods. Cell growth was assessed by a $^3$H-thymidine incorporation assay as described in Materials and Methods.

Since earlier studies indicated that variation of serum concentration affects ceramide-mediated growth inhibition,(26, 35) Jurkat cell growth inhibition in cells cultured in the presence of ceramide and/or paclitaxel with varying amounts of serum was investigated (FIG. 2). Ceramide-mediated growth inhibition was more pronounced (>99%) at low serum (1%) levels compared with that observed in high serum (≧5%) conditions. Growth inhibition in cultures treated with paclitaxel alone was unaffected by variation of serum levels from 10% to 1%. Combination of paclitaxel (0.6 ng/ml) and ceramide in 10% serum inhibited growth ≧61% more than paclitaxel alone (n=5) (FIG. 2).

Figure 3A:
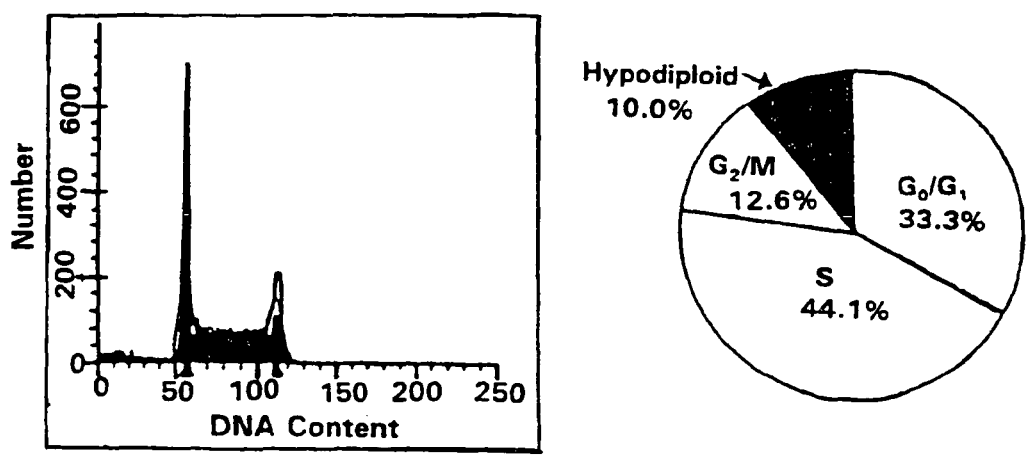
FIGS. 3A-3F. Cell-cycle analysis of Jurkat cells in the presence of paclitaxel and/or ceramide. Cell-cycle analysis was performed at 24 hours because, by 48 and 72 hours, most of the cells (treated with a combination of paclitaxel and ceramide) were hypodiploid, and accurate assessment of the percentage of cells in $G_0$-$G_1$, S- and $G_2$-M phases could not be made. Propidium iodide (0.05 mg/ml) was added to cell cultures in a total volume of 0.5 ml. Samples were analyzed by FACScan (Becton Dickinson, Costa Mesa, Calif.). Cell-cycle distribution was calculated as a percentage of the total population of both live and hypodiploid cells.
Figure 3B:
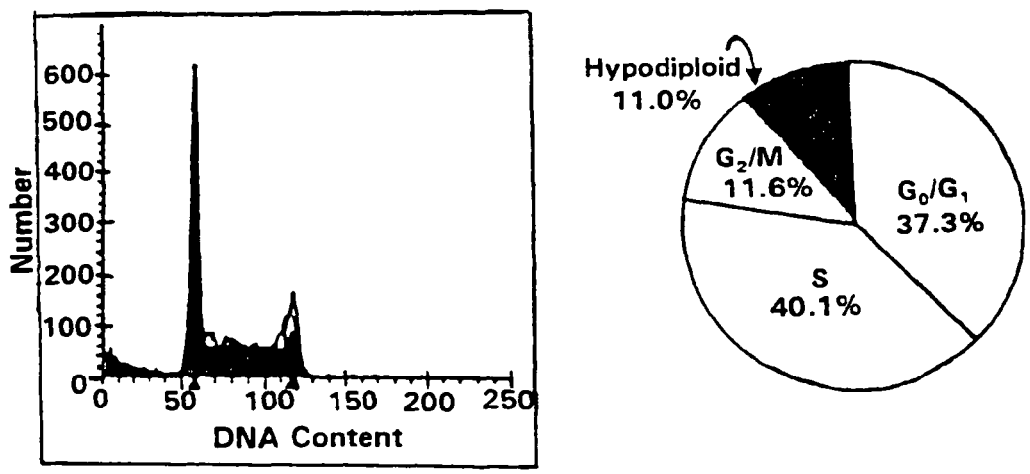

In the next series of experiments it was sought to establish the effect of ceramide on paclitaxel-induced arrest of cell cycle growth measured at 24 hours (FIGS. 3A-3F). Analysis of untreated Jurkat cells at the beginning of culture revealed that 51.7% of the cell population was in $G_0$-$G_1$ phase, 32.9% in S phase, and 9.4% in $G_2$-M phase (data not shown). After 24 hours, the percentage of cells in $G_0$-$G_1$ decreased by 18.4% with a concurrent equivalent S-phase augmentation, which suggested significant cell growth after the addition of fresh culture medium (FIG. 3A). The cell cycle pattern following ceramide treatment in the presence of 10% fetal bovine serum did not differ from the non-ceramide-exposed control at 24 hours (FIG. 3B).

Figure 3C:
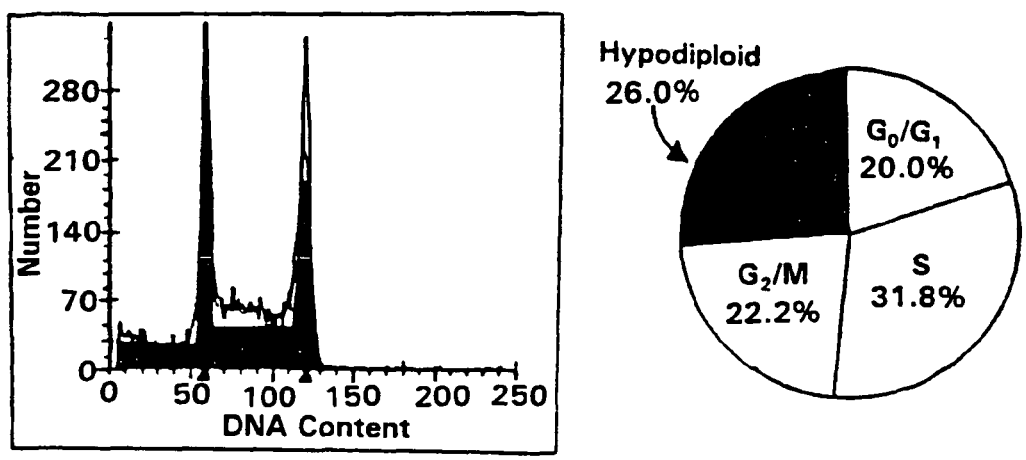
Figure 3D:
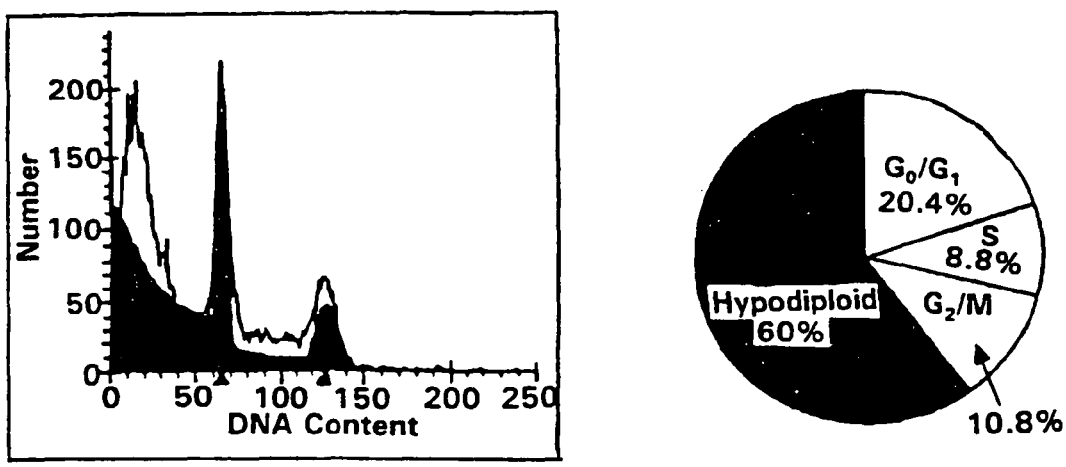
Figure 3E:
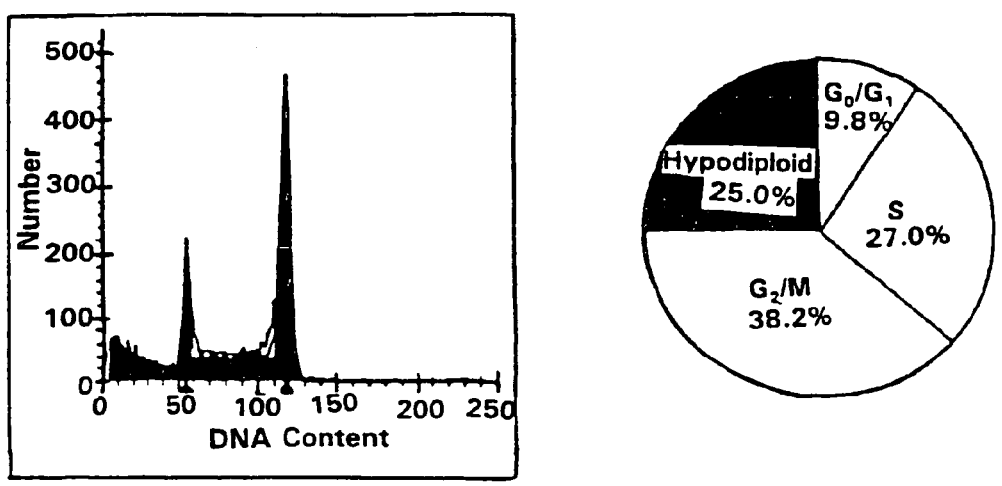
Figure 3F:
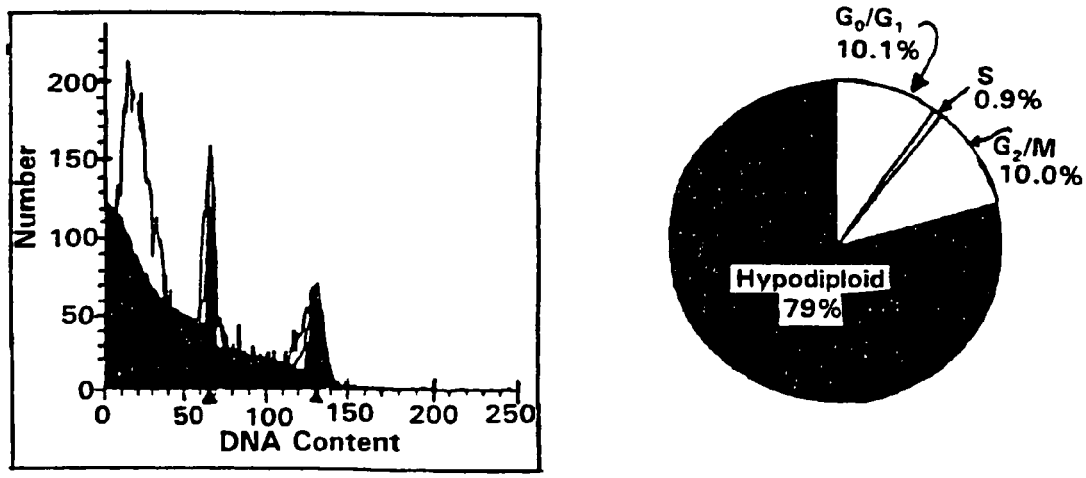
Figure 4A:
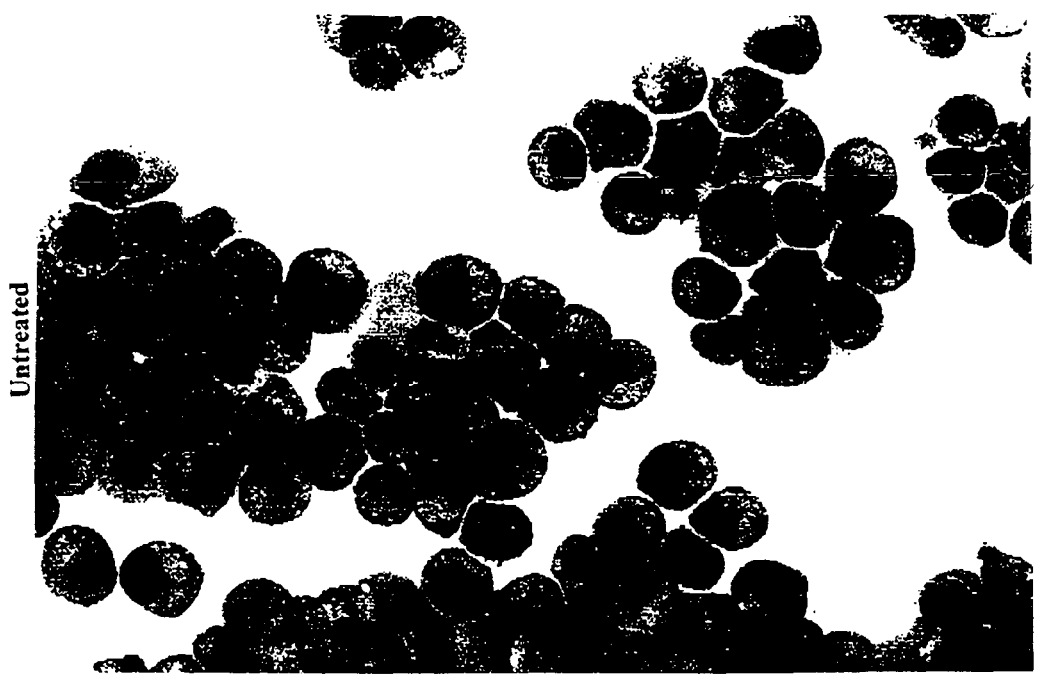
FIGS. 4A-4F. Wright's stain analysis of Jurkat cells treated with paclitaxel and ceramide. Morphology of paclitaxel- and ceramide-induced apoptosis in Jurkat cells stained with Giemsa/Wright at 48 hours.
Figure 4B:
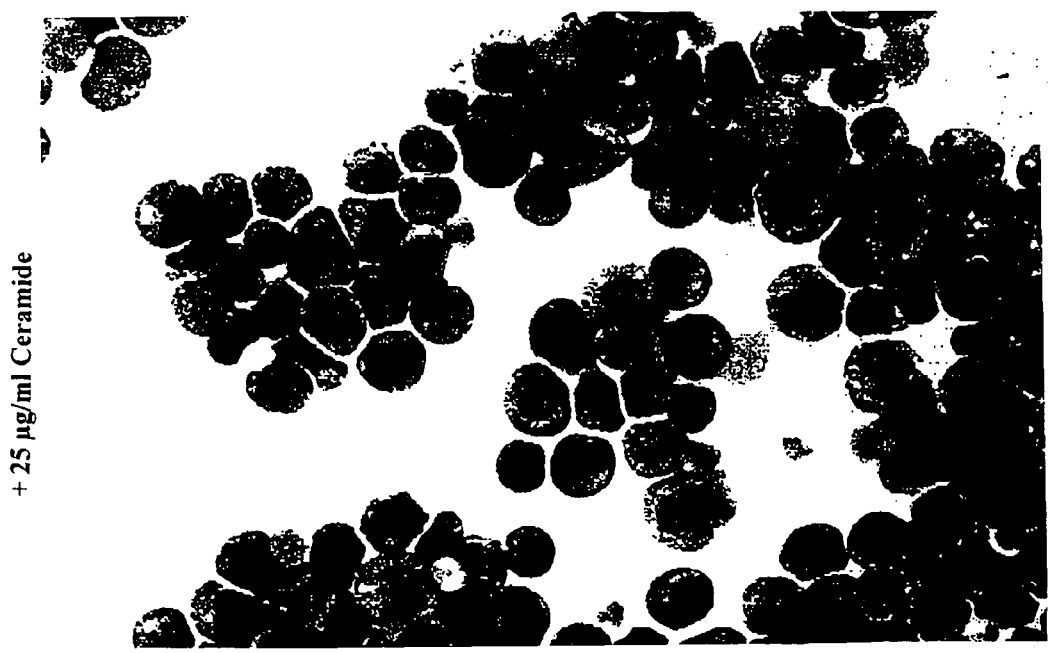
Figure 4C:
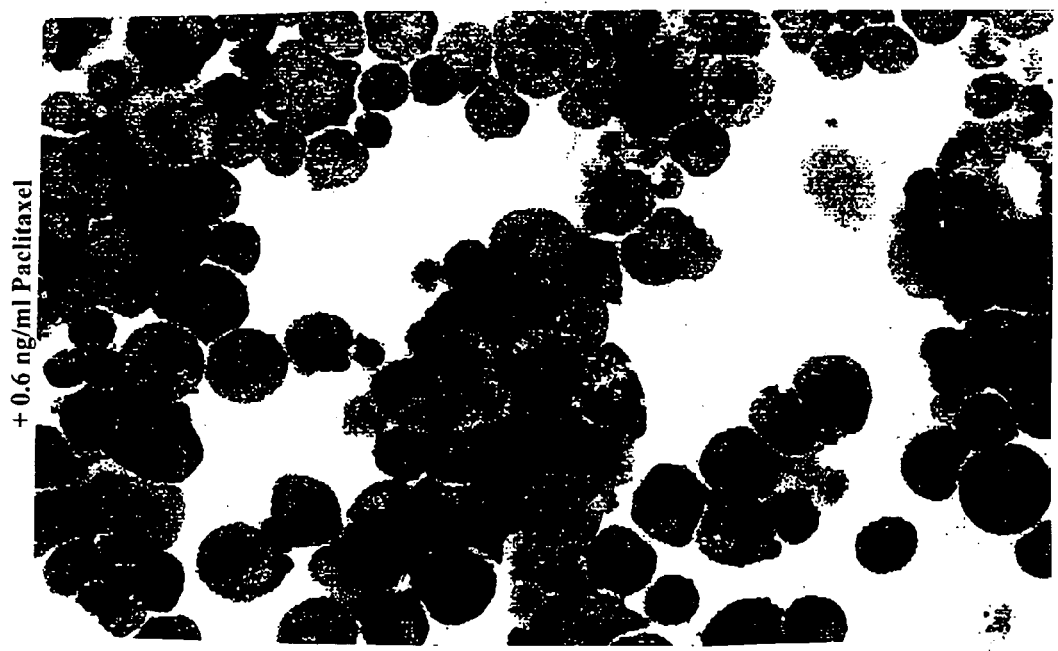
Figure 4D:
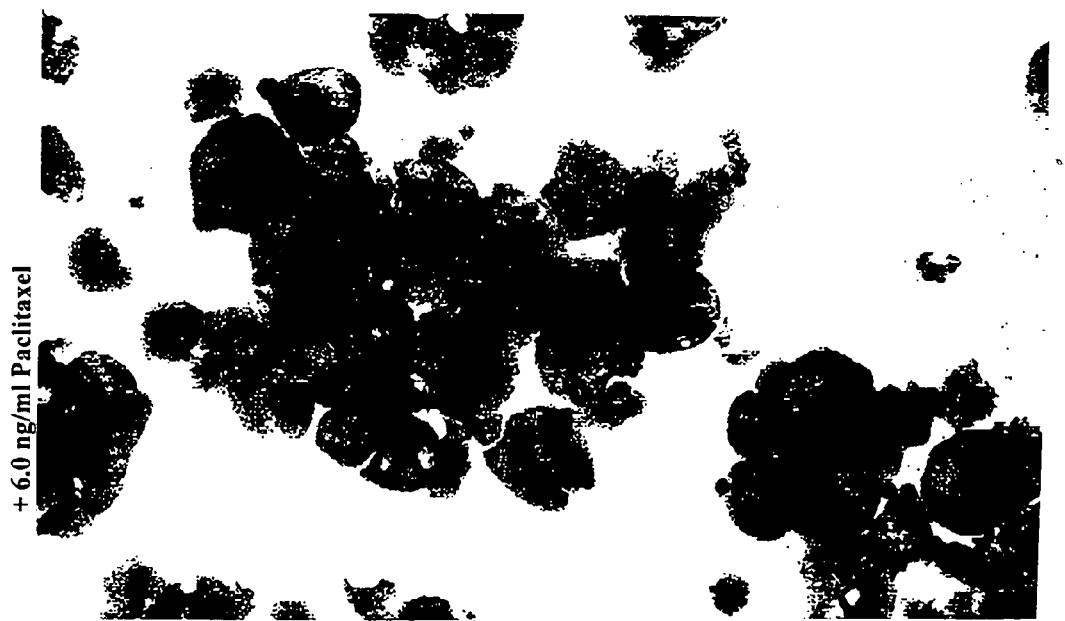
Figure 4E:
Figure 4F:
Figure 5A:
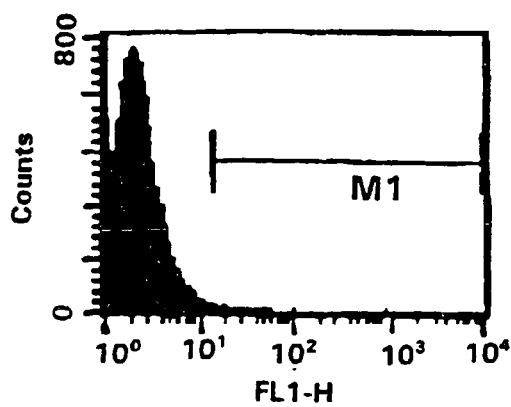
FIGS. 5A-5H. TUNEL assay for the measurement of paclitaxel- and ceramide-induced Jurkat cell apoptosis. TUNEL assay was performed at both 24 (panel A) and 48 (panel B) hours. Apoptotic cells are demonstrated by the area M1.
Figure 5B:
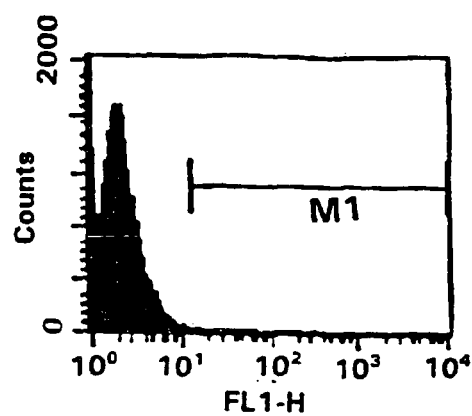
Figure 5C:
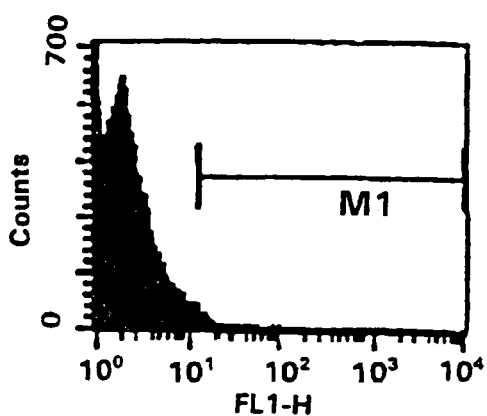
Figure 5D:
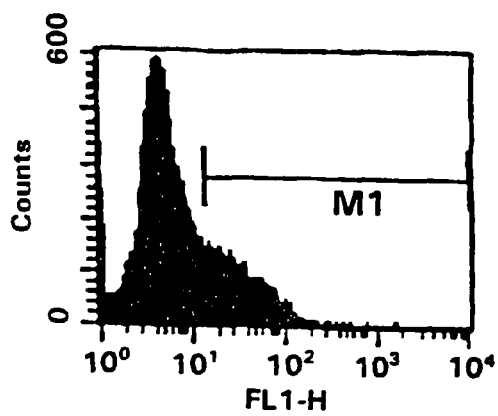
Figure 5E:
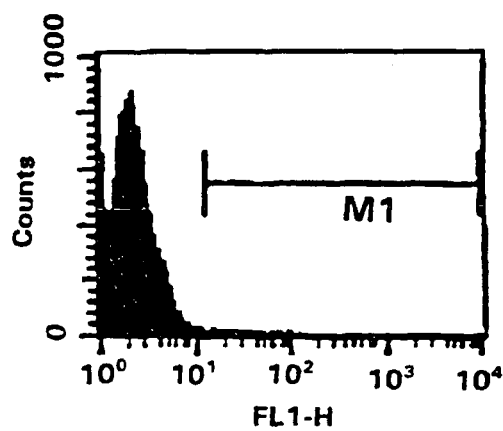
Figure 5F:
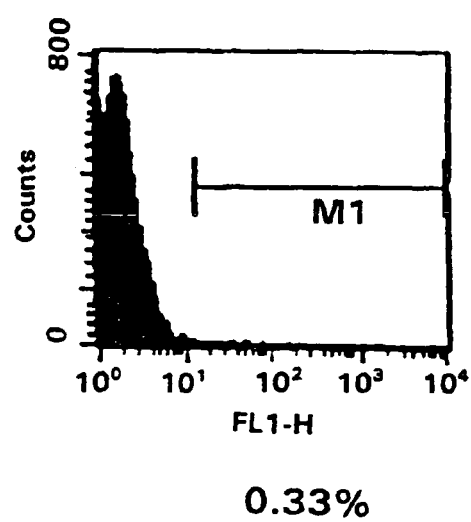
Figure 5G:
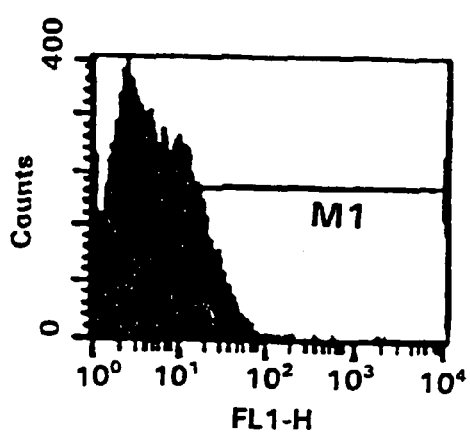
Figure 5H:
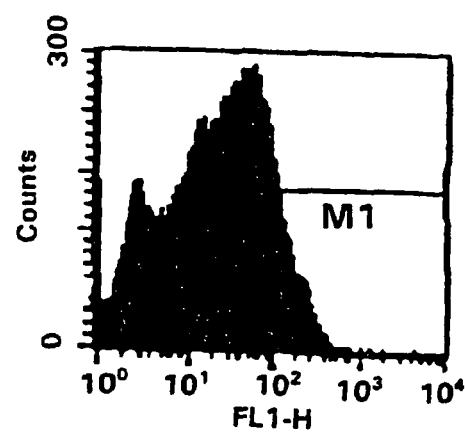

The addition of 0.6 or 6.0 ng/ml paclitaxel alone at 24 hours resulted in the accumulation of 22.2% and 38.2%, respectively, of the total cell population in the $G_2$-M phase compared with 12.6% of the untreated cell control. This 2-3 fold increase in the $G_2$-M cell population was followed by 13.3% or 23.5% decrease of cells in the $G_0$-$G_1$ phase, thus confirming the known action of paclitaxel (FIGS. 3C and 3E). In Jurkat cells treated with a combination of either 0.6 or 6.0 ng/ml paclitaxel and ceramide, cell populations decreased to approximately 10% in $G_2$-M phase and 8.8% and 0.9% in S phase (in contrast to 31.8% and 27% with paclitaxel alone). Therefore combined treatment seems to eliminate cells from the S- and $G_2$-M phases (FIGS. 3D and 3F).

Flow-cytometric analysis also indicated the presence of hypodiploid (sub-$G_1$) cell population (FIGS. 3A-3F). Compared with untreated control values of 10%, treatment with 0.6 and 6.0 ng/ml paclitaxel each resulted in hypodiploid populations of approximately 25%. The addition of ceramide to paclitaxel-treated cultures demonstrated a substantial accumulation (to 60%-79%) of hypodiploid cells. These findings indicate that low thymidine uptake in combined paclitaxel and ceramide-treated cultures is not only the consequence of cell growth arrest but also possibly of cell death.

To observe the morphological changes induced by paclitaxel, ceramide, and their combination, a Wright's stain analysis of sample cultures was performed after 48 hours' treatment (FIG. 4). FIG. 4A illustrates the morphological features of normal Jurkat cells at 48 hours. A high nuclear-to-cytoplasmic ratio was evident, and all cell membranes were intact with abundant cytoplasmic granules present. Ceramide-treated cell populations were morphologically indistinguishable from control cells in 10% serum (FIG. 4B). In contrast, apoptotic bodies were noted amid cell shrinkage and nuclear and membrane blebbing following treatment with 0.6 and 6.0 ng/ml of paclitaxel alone (FIGS. 4C and 4D). When ceramide and 0.6 and 6.0 ng/ml of paclitaxel were added in combination, more extensive features of cell death, including a loss of cell membrane and cytoplasmic contents, were apparent (FIGS. 4E and 4F).

The presence of apoptosis in Jurkat cells treated with 0.6 ng/ml of paclitaxel, 12.5 or 25 µg/ml of ceramide, and combinations of both agents was confirmed by TUNEL assay at 24 and 48 hours. Apoptosis in Jurkat cells treated with either 0.6 ng/ml of paclitaxel or 12.5 and 25 µg/ml of ceramide alone was almost undetectable (≦3%) at 24 hours. At 48 hours, exposure of Jurkat cells to 0.6 ng/ml of paclitaxel resulted in 19.6% apoptosis, but no significant apoptosis (0.41% and 0.33%) was observed in samples treated with 12.5 and 25 µg/ml of ceramide, respectively, at 48 hours. The combination of 0.6 ng/ml of paclitaxel and 25 µg/ml of ceramide resulted in 25.5% and 66.1% TUNEL-positive cells at 24 and 48 hours, respectively, demonstrating supra-additive enhancement of cell death (FIGS. 5A-5H).

Discussion

Although synergy between paclitaxel and many other chemotherapeutic agents, such as vincristine and etoposide,[31-33] has proven effective in cancer cell growth inhibition, this study is the first to characterize ceramide enhancement of paclitaxel-mediated growth inhibition. Paclitaxel-induced cell growth inhibition of Jurkat leukemic cells occurred optimally at an $ED_{50}$ of approximately 0.5 ng/ml, in agreement with widely cited findings that identify paclitaxel as a growth-inhibitory agent for many human leukemic cell lines.[36-39] Furthermore, it was observed that the level of growth inhibition by ceramide depends on serum concentration. The observation of the absence of ceramide-induced cell growth inhibition in 10% serum in Jurkat T cells paralled studies that showed a reduction in ceramide-induced cell growth inhibition in cell lines CMK-7, HL-60, and U937.[35] Interestingly, the enhancement of paclitaxel action by ceramide was not affected by high serum concentrations.

Paclitaxel and ceramide have been reported to arrest the growth of cells in the $G_2$-M and $G_0$-$G_1$ phases of the cell cycle, respectively.(12, 13, 25-27) In the cell cycle studies described herein, the percentage of cells in $G_0$-$G_1$ was almost identical in both ceramide-treated and untreated cell cultures, consistent with the lack of effect on $^3$H-thymidine uptake under these conditions. A significant change was found in the percentage of cells in S phase after paclitaxel treatment, indicating the loss of active DNA synthesis by Jurkat cells. The hypodiploid population of cells treated with the combination of paclitaxel and ceramide increased significantly compared to those treated with paclitaxel or ceramide alone. Paclitaxel addition at 0.6 and 6.0 ng/ml yielded $G_2$-M/$G_0$-$G_1$ ratios of 1.11 and 3.9, respectively, consistent with the known action of paclitaxel as a $G_2$-M blocker of the cell cycle.(12,13) Combinations of paclitaxel (0.6 and 6.0 ng/ml) and ceramide (25 µg/ml) demonstrated $G_2$-M/$G_0G_1$ ratios of 0.54 and 1.0, respectively, indicating that the cell population being eliminated was also from the $G_2$-M phase, in addition to S phase, resulting in cell death. These results were consistent with TUNEL assay and also by histological evaluation utilizing the Giemsa-Wright(40) staining technique.

Previous studies have demonstrated activation of Fas expression on leukemic cells by another mitotic spindle agent, vincristine, which differs from paclitaxel in that it acts by degrading the mitotic spindle in $G_2$-M phase.(28-30) Ceramide enhancement of paclitaxel-mediated apoptosis may possibly be attributed to a mechanism similar to that of the activation of Fas on the surface of Jurkat cells.(15,22,41-42) It is hypothesized that paclitaxel enhances intracellular ceramide production by increasing acid sphingomyelinase activity by the engagement of either Fas receptor or another homologous TNF receptor such as DR4.(43) This enhancement of intracellular ceramide levels is further augmented by the addition of exogenous ceramide. Recent studies have shown that paclitaxel is capable of upregulating Fas ligand expression.(29,44) It may be possible that paclitaxel/ceramide mediated enhancement is due to upregulation and release of Fas ligand from the surface of Jurkat cells and into the surrounding cell culture media, which can then induce cellular suicide by ligating Fas on the cell membrane. Such a mechanism has been proposed in activation-induced death of Jurkat cells whereby APO2/TRAIL ligand, a TNF homologue, binds to newly discovered DR4 receptor.(43)

While the role of Fas mediated events during paclitaxel exposure is unknown, recent reports have disputed the role of the generation of ceramide in apoptosis by suggesting that ceramide is either not involved in Fas-mediated apoptosis or is not a critical component of the initial apoptotic events and may instead act downstream of the cascade.(45-47) However, none of these studies measured intracellular ceramide levels at high serum concentrations, which, the present study shows, may profoundly affect the role in leukemic cell apoptosis. The present study suggests that cell apoptosis mediated by paclitaxel and ceramide may be linked by a common signal transducing pathway leading to cell death.

REFERENCES FOR FIRST SERIES OF EXPERIMENTS

1. Slichenmyer, W. J., Von Hoff D. D., Taxol: a new and effective anti-cancer drug. *Anticancer Drugs*, 1991, 2, 519.
2. Zoli, W., Flamigni, A., Frassineti, G. L., Bajorko, P., De Paola, F., Milandri, C., Amadori, D., Gasperi-Campani, A.: In vitro activity of taxol and taxotere in comparison with doxorubicin and cisplatin on primary cell cultures of human breast cancers. *Breast Cancer Res. Treat.*, 1995, 34, 63.
3. McGuire, W. P., Rowinsky, E. K., Rosenshein, N. B., Grumbine, F. C., Ettinger, D. S., Armstrong, D. K., Donehower, R. C., Taxol: a unique antineoplastic agent with significant activity in advanced ovarian epithelial neoplasms. *Ann. Int. Med.*, 1989, 111, 273.
4. Silvestrini, R., Zaffaroni, N., Orlandi, L., Oriana, S.: In vitro cytotoxic activity of Taxol and Taxotere on primary cultures and established cell lines of human ovarian cancer. *Stem Cells (Dayt)*, 1993, 11, 528.
5. Yamori, T., Sato, S., Chikazawa, H., Kadota, T.: Anti-tumor efficacy of paclitaxel against human lung cancer xenografts. *Jpn. J. Cancer Res.*, 1997, 88, 1205.
6. Akutsu, M., Kano, Y., Tsunoda, S., Suzuki, K., Yazawa, Y., Miura, Y.: Schedule-dependent interaction between paclitaxel and doxorubicin in human cancer cell lines in vitro. *Eur. J. Cancer*, 1995, 31A, 2341.
7. Elomaa, L., Joensuu, H., Kulmala, J., Klemi, P., Grenman, R.: Squamous cell carcinoma is highly sensitive to taxol, a possible new radiation sensitizer. *Acta Otolaryngol. (Stockh)*, 1995, 115, 340.
8. Spencer, C. M., Faulds, D., Paclitaxel: a review of its pharmacodynamic and pharmacokinetic properties and therapeutic potential in the treatment of cancer. *Drugs*, 1994, 48, 794.
9. Huizing, M. T., Misser, V. H., Pieters, R. C., ten Bokkel Huinink, W. W., Veenhof, C. H., Vermorken, J. B., Pinedo, H. M., Beijnen, J. H., Taxanes: a new class of antitumor agents. *Cancer Invest.*, 1995, 13, 381.
10. Rowinsky, E. K., Donehower, R. C., Jones, R. J., Tucker, R. W., Microtubule changes and cytotoxicity in leukemic cell lines treated with taxol. *Cancer Res.*, 1988, 48, 4093.
11. Kumar, N., Taxol-induced polymerization of purified tubulin. Mechanism of action. *J. Biol. Chem.*, 1981, 256, 10435.
12. Milross, C. G., Mason, K. A., Hunter, N. R., Chung, W. K., Peters, L. J., Milas, L., Relationship of mitotic arrest and apoptosis to antitumor effect of paclitaxel. *J. Natl. Cancer Inst. Monograph*, 1996, 88, 1308.
13. Milas, L., Hunter, N. R., Kurdoglu, B., Mason, K. A., Meyn, R. E., Stephens, L. C., Peters, L. J., Kinetics of mitotic arrest and apoptosis in murine mammary and ovarian tumors treated with taxol. *Cancer Chemother. and Pharmacol.*, 1995, 35, 297.
14. Gangemi, R. M., Costa, G., Fulco, R. A., d'Aquino, S., Aronadio, O., Apoptosis susceptibility of human carcinoma and leukemia cell lines to taxol. Relationship with cell cycle and drug concentration. *Ann. N.Y. Acad. Sci.*, 1996, 784, 550.
15. Cifone, M. G., De Maria, R., Roncaioli, P., Rippo, M. R., Azuma, M., Lanier, L. L., Santoni, A., Testi, R., Apoptotic signalling through CD95 (Fas/Apo-1) activates an acidic sphingomyelinase. *J Exp Med.*, 1994, 180, 1547.
16. Testi, R., Sphingomyelin breakdown and cell fate. *Trends in Biochem Sci*, 1996, 21, 468.
17. Jarvis, W. D., Grant, S., and Kolesnick, R. N., Ceramide and the induction of apoptosis. *Clin Cancer Res.*, 1996, 2, 1.
18. Obeid, L. M., Hannun, Y. A., Ceramide: a stress signal and mediator of growth supression and apoptosis. *J Cell Biochem.*, 1995, 58, 191.
19. Obeid, L. M., Linardic, C. M., Karolak, L. A., Hannun, Y. A., Programmed cell death induced by ceramide. *Science*, 1993, 259, 1769.
20. Ji, L., Zhang, G., Uematsu, S., Akahori, Y., Hirabayashi, Y., Induction of apoptotic DNA fragmentation and cell death by natural ceramide. *FEBS Letters*, 1995, 358, 211.
21. Hannun, Y. A., Obeid, L. M., Ceramide: an intracellular signal for apoptosis. *Trends in Biochem Sci*, 1995, 20, 73.
22. Tepper, C. G., Jayadev, S., Liu, B., Bielawska, A., Wolff, R., Yonehara, S., Hannun, Y. A., Seldin, M. F., Role for ceramide as an endogenous mediator of Fas-induced cytotoxicity. *Proc. Natl. Acad. Sci.*, 1995, 92, 8443.

23. Kolesnick, R. N., Haimovitz-Friedman, A., Fuks, Z., The sphingomyelin signal transduction pathway mediates apoptosis for tumor necrosis factor, Fas, and ionizing radiation. *Biochem. and Cell Biol.*, 1994, 72, 471.
24. Jarvis, W. D., Kolesnick, R. N., Formari, F. A., Traylor, R. S., Gewirtz, D. A., and Grant, S., Induction of apoptotic DNA damage and cell death by activation of the sphingomyelin pathway. *Proc. Natl. Acad. Sci.* 1994, 91, 73.
25. Kuroki, J., Hirokawa, M., Kitabayashi, A., Lee, M., Horiuchi, T., Kawabata, Y., Miura, A. B., Cell-permeable ceramide inhibits growth of B lymphoma Raji cells lacking TNF-alpha receptors by inducing $G_0/G_1$ arrest but not apoptosis: a new model for dissecting cell-cycle arrest and apoptosis. *Leukemia*, 1996, 10, 1950.
26. Jayadev, S., Liu, B., Bielawska, A. E., Lee, J. Y., Nazaire, F., Pushkareva, M. Yu, Obeid, L. M., Hannun, Y. A., Role for ceramide in cell cycle arrest. *J. Biol. Chem.*, 1995, 270, 2047.
27. Venable, M. E., Lee, J. Y., Smyth, M. J., Bielawska, A., Obeid, L. M., Role of Ceramide in Cellular Senescence. *J. Biol. Chem.*, 1995, 270, 30701.
28. Hirose, Y., Takiguchi, T., Microtubule changes in hematologic malignant cells treated with paclitaxel and comparison with vincristine cytotoxicity. *Blood Cells and Mol. Dis.*, 1995, 21, 119.
29. Roth, W., Fontana, A., Trepel, M., Reed, J. C., Dichgans, J., Weller, M., Immunochemotherapy of malignant glioma: synergistic activity of CD95 ligand and chemotherapeutics. *Cancer Immunol. and Immunotherapy*, 1997, 44, 55.
30. Efferth, T., Fabry, U., Osieka, R., Anti-Fas/Apo-1 monoclonal antibody CH-11 depletes glutathione and kills multidrug-resistant human leukemic cells. *Blood Cells and Mol. Dis.*, 1996, 22, 2.
31. Curtis, J. E., Minkin, S., Minden, M. D., McCulloch, E. A., A role for paclitaxel in the combination chemotherapy of acute myeloblastic leukaemia: preclinical cell culture studies. *Br. J. Haematol.*, 1996, 95, 354.
32. Brooks, D. J., Alberts, D. S., A phase I study of etoposide phosphate plus paclitaxel. *Sem. Oncol*, 1996, 23, 33.
33. Knick, V. C., Eberwein, D. J., Miller, C. G., Vinorelbine tartrate and paclitaxel combinations: enhanced activity against in vivo P388 murine leukemia cells. J. Natl. Cancer Inst. Monograph, 1995, 87, 1072.
34. Look, A. T., Melvin, S. L., Williams, D. L., Brodeur, G. M., Dahl, G. V., Kalwinsky, D. K., Murphy, S. B., Mauer, A. M., Aneuploidy and percentage of S-phase cells determined by flow cytometry correlate with cell phenotype in childhood acute leukemia. *Blood*, 1982, 60, 959.
35. Sweeney, E., Sakakura, C., Shirahama, T., Masamune, A., Ohta, H., Hakomori, S., Igarashi, Y., Sphingosine and its methylated derivative N,N dimethyl-sphingosine (DMS) induce apoptosis in a variety of human cancer cell lines. *Int. J. Cancer*, 1996, 66, 358.
36. Rowinsky, E. K., Burke, P. J., Karp, J. E., Tucker, R. W., Ettinger, D. S., Donehower, R. C.: Phase I and pharmacodynamic study of taxol in refractory acute leukemias. *Cancer Res.*, 1989, 49, 4640.
37. Li, X., Gong, J., Feldman, E., Seiter, K., Traganos, F., Darzynkiewicz, Z., Apoptotic cell death during treatment of leukemias. *Leukemia and Lymphoma*, 1994, 13 Suppl 1, 65.
38. Gangemi, R. M., Tiso, M., Marchetti, C., Severi, A. B., Fabbi, M., Taxol cytotoxicity on human leukemic cell lines is a function of their susceptibility to programmed cell death. *Cancer Chemotherapy and Pharmacol.*, 1995, 36, 385.
39. Auber, M. L., Horwitz, L. J., Blaauw, A., Khorana, S., Tucker, S., Woods, T., Warmuth, M., Dicke, K. A., McCredie, K. B., Spitzer, G.: Evaluation of drugs for elimination of leukemic cells from the bone marrow of patients with acute leukemia. *Blood*, 1988, 71, 166.
40. Ray, S., Ponnathpur, V., Huang, Y., Tang, C., Mahoney M E, Ibrado A M, Bullock G, Bhalla, K., 1-beta-D-arabinofuranosylcytosine-, mitoxantrone-, and paclitaxel-induce apoptosis in HL-60 cells: Improved method for detection of internucleosomal DNA fragmentation. *Cancer Chemotherapy and Pharmacol.*, 1994, 34, 365.
41. Ballou, L., Laulederkind, S., Rosloniec, E; Raghow, R: Ceramide signalling and the immune response. *Biochim. et Biophys. Acta.*, 1996, 1301, 273.
42. Herr, I., Wilhelm, D., Böhler, T., Angel, P., Debatin, K. M., Activation of CD95 (APO-1/Fas) signaling by ceramide mediates cancer therapy-induced apoptosis. *EMBO J.*, 1997, 16, 6200.
43. Martinez-Lorenzo, M. J., Alava, M. A., Gamen, S., Kim, K. J., Chuntharapai, A., Piniero, A., Naval, J., Anel, A., Inovlvement of $APO_2$ ligand/TRAIL in activation-induced death of Jurkat and human peripheral blood T cells. *Eur. J. Immunol.* 1998, 28, 2714.
44. Roth, W., Wagenknecht, B., Grimmel, C., Dichgans, J., Weller, M., Taxol-mediated augmentation of CD95 ligand-induced apoptosis of human malignant glioma cells: association with bcl-2 phosphorylation but neither activation of p53 nor G2/M cell cycle arrest. *Br. J. Cancer,* 1998, 77, 404.
45. Sillence, D. J., Allan, D., Evidence against an early signalling role for ceramide in Fas-mediated apoptosis. *Biochem. Journal*, 1997, 15, 29.
46. Watts, J. D., Gu, M., Polyerino, A. J., Patterson, S. D., Aebersold, R., Fas-induced apoptosis of T cells occurs independently of ceramide generation. *Proc. Natl. Acad. Sci.* 1997, 94, 7292.
47. Hsu, S-C, Wu, C-C, Luh, T-Y, Chou, C-K, Han, S-H, Lai, M-Z, Apoptotic signal of Fas is not mediated by ceramide. *Blood*, 1998, 91, 2658.

2nd Series of Experiments

Effects of Paclitaxel and Ceramide on Human Squamous Carcinoma Cell Line Tu138 in Vitro and in Vivo The purpose of this study was to observe in vitro and in vivo effects (additive or synergistic) of combining paclitaxel and ceramide in inducing cytotoxicity and apoptosis in human squamous carcinoma cells (Tu138). Synergistic cytotoxic and apoptic action of these two agents in vitro in other neoplastic cell lines have been previously demonstrated.

Methods

The effects of paclitaxel and ceramide on cell growth of Tu138 was evaluated by MTT dye assay (see infra p. 35), cell cycle progression by flow cytometry (see infra pp. 35-36), cell apoptosis by TUNEL assay (see infra pp. 35-36) and tumor growth and weight in nude mice (see infra pp. 37-38). To corroborate in vitro findings Tu138 cells were planted subcutaneously on nude mice. Treatment with paclitaxel (120 µg/0.1 mL)+ceramide (500 µg/0.2 mL) was begun on day 4 with thrice weekly injections administered subcutaneously near the tumor site for 5 weeks. Other treatment groups included: vehicle only, paclitaxel alone and ceramide alone. Tumor size was measured once a week. All groups of mice were sacrificed on day 45 and excised tumors were weighed.

Results

Cell growth studies showed synergystic growth inhibition with paclitaxel+ceramide and was confirmed by a 50% isobologram analysis in six separate experiments (p value <0.05). The TUNEL assay also confirmed enhanced apoptosis by the combined treatments. Cell cycle progression studies suggested that the target population of cells was either in the S or $G_2$-M phase of the cell cycle. Preliminary in vivo studies showed equivalent growth of Tu138 cell-tumor in control and paclitaxel treated mice whereas the ceramide injected group showed a slight decrease in tumor size at week 5. The paclitaxel+ceramide group showed a decline of 70% in tumor size compared to control group. There was also significant reduction in tumor weight (88% in paclitaxel+ceramide group vs. control). The ceramide only group also had a substantial reduction in tumor weight. The excised tumors are being studied to determine tumor cell morphology and cellular apoptosis.

Discussion

Paclitaxel and ceramide are synergistic in inducing apoptosis and cytotoxicity in the Tu138 squamous cell line in vitro. In vivo effects on tumor growth and weight are similar suggesting preclinical therapeutic potential of these agents.

3rd Series of Experiments

Combined Cytotoxic Action of Paclitaxel (Taxol) and Ceramide on Human Tu138 Squamous Carclnoma Cell Line of the Head and Neck Increased intracellular ceramide levels can be induced by a variety of agents including TNFα, Fas, ionizing radiation and chemotherapeutic agents causing apoptosis in several cell systems. Exogenous ceramide can also induce apoptosis by raising intracellular levels. Paclitaxel (taxol), a highly efficacious chemotherapeutic drug, used in the treatment of recalcitrant ovarian and breast as well as other neoplasms, is now undergoing Phase II trials in squamous cell carcinoma of the head and neck. This study shows that paclitaxel and ceramide both induce apoptosis in a human squamous carcinoma cell line Tu138, with an $ED_{50}$ of 1920±1200 ng/ml and 22±5 µg/ml respectively. Ceramide combined with paclitaxel induced cytotoxic effects which were synergistic in greater than 75% of the experimental combinations tested, based on isobologram analysis. The synergy in cell kill was confirmed by TUNEL assay. Flow cytometric analysis of the combination treatment indicated elimination of Tu138 cells from S and/or $G_2$-M phases of the cell cycle. This synergistic combination may have therapeutic application in the treatment of head and neck cancer. The mechanism of synergistic action between these two agents may involve a commonality in signal transduction pathways induced by paclitaxel and ceramide.

Sphingolipids have been shown to be biologically active and have numerous regulatory effects on cell function including cell growth and differentiation. A number of inducers of sphingomyelin hydrolysis causing concommittant elevation of intracellular ceramide have been identified. These include TNFα, endotoxins, interferon α, IL-1, Fas ligand, CD28, chemotherapeutic agents, heat and ionizing radiation (1, 2). The kinetics of endogenous ceramide formation and accumulation appear to be complex and variable in different cell systems and with different inducers of sphingomyelin catabolism (3-6). It has recently been established that endogenously generated ceramide acts as a second messenger and induces apoptosis (7). Ceramide synthesis de novo has been implicated in lethal responses to several chemotherapeutic agents such as anthracyclines (8) and ara-C (9). Many recent studies have examined the effect of exogeneous ceramide on the induction of apoptosis in a variety of tumor cells. Ceramide has been shown in such cases to cause cell cycle arrest in several cell lines as well as apoptosis, cell senescence and terminal differentiation (10-13).

Paclitaxel is a chemotherapeutic drug with ability to block growing cells in the $G_2$-M phase of the cell cycle (14). This is due to the fact that paclitaxel treated cells cannot undergo the microtubule depolymerization step to cytokinesis. In addition many paclitaxel mediated effects are known including bcl-2 phosphorylation (15) and the involvement of apoptosis via BAX, a bcl-2 dimerization product (16). Paclitaxel is currently being used in a variety of different cancers in clinical trials, alone and in combination with a variety of chemotherapeutic agents. (17-18) and has been shown to induce high rates of clinical responses in patients with squamous cell cancer of the head and neck (19). Neurotoxicity and myelosuppression seem to be the major limiting factors associated with paclitaxel treatment, hence there have been numerous studies combining other drug therapies with paclitaxel to increase its therapeutic efficacy. The purpose of the present studies was to examine if paclitaxel induced apoptosis can be enhanced by the addition of exogeneously added ceramide.

Materials and Methods

Tumor Cell Line:

Tu138, an adherent squamous carcinoma cell line of the head and neck was established at U T M D Anderson Cancer Center, Houston, Tex. (20, 21) and was generously provided by Dr. Gary Clayman's laboratory. Tu138 cells were maintained routinely in T-75 culture flasks (Falcon, Inc., N.J.) at a plating cell density of $0.1 \times 10^6$ per 75 sq. cm. surface area in complete D-MEM/F-12 culture medium (10 ml) containing 10% fetal bovine serum (FBS, Atlanta Biologicals, Ga.), 2 mM glutamine (Gibco, N.Y.), 50 units/mL penicillin, 50 mg streptomycin (Gibco, N.Y.) and 20 mM Hepes (Sigma, Mo.) in a 5% $CO_2$ atmosphere at 37° C. Tu138 cells were replenished with fresh complete culture medium twice weekly until confluence.

Treatment of Tu138 Tumor Cell Line with Drugs

For exposures to paclitaxel (taxol) and/or ceramide Tu138 cells were trypsinized in 0.25% trypsin-EDTA solution, washed twice in DMEM and plated in 96-well culture plates at a concentration of $2 \times 10^4$ in a final volume of 0.2 ml in D-MEM/F-12 with 10% FBS and incubated in the presence or absence of different concentrations of paclitaxel (Taxol) (0-6000 ng/ml; Bristol Myers Squibb, Inc., N.J.) and/or ceramide (N-hexanoyl-D-sphingosine, 0-25 µg/ml; Sigma Chemicals, Mo.). At the indicated times (24 to 72 hours), cells were subjected to (a) tetrazolium-based dye assay for cell survival measurements, (b) flow cytometry analysis for cell cycle progression and (c) measurements of apoptosis by TUNEL assay.

MTT Assay

For the measurement of cellular cytotoxicity, 50 µl of 0.2% solution of MTT [3-(4,5-dimethyl-thiazol-2-yl)-2,5-diphenyltetrazolium bromide] dye (Sigma Chemicals, Mo.) was added to Tu138 cells after treatment with paclitaxel and/or ceramide and incubated at 37° C. (22). At the end of an incubation period of 4 hours, culture plates were centrifuged at 300 g for 2 minutes. After removal of the culture medium, 150 µl of DMSO was added to solubilize MTT formazan crystals formed by cells undergoing coupled respiration and optical density was determined by the use of ELISA reader (Model EL 311, Biotek Inc.) at 540 nm.

Cell Cycle Measurements and TUNEL Assay

In concurrence with the MTT dye assay, Tu138 cells were plated in 6-well culture dishes at a concentration of $2\times10^6$ in a volume of 4 ml in D-MEM/F-12 containing 10% FBS at 37° C. and exposed to paclitaxel (600 ng/ml) and/or ceramide (25 µg/ml). At the end of either 24 or 48 hours, cells were trypsinized and washed with the culture medium. For cell cycle measurements, cells were mixed with 0.5 ml of 0.1% propidium iodide solution (New Concepts Scientific Ltd. ON) containing 0.1% sodium citrate and 0.1% NP-40. RNase (1 µg) was added to each sample and cells were incubated at 4° C. for 30 minutes. At least $1\times10^4$ cells were acquired on a precalibrated FACScan (Beckton Dickinson, Calif.) flow cytometer. For precalibration "DNA QC" (Becton Dickinson, Calif.) kit was utilized. The acquired cells were then subjected to cell cycle analysis by the use of "Modfit LT" software (Beckton Dickinson, Calif.). For measurements of apoptosis, In Situ Cell Death Detection Kit (Boehringer Manheim, Ind.) followed by flow cytometry analysis was utilized.

Results

Paclitaxel and Ceramide Induced Cytotoxicity as a Function of Time of Exposure

Figure 6A:
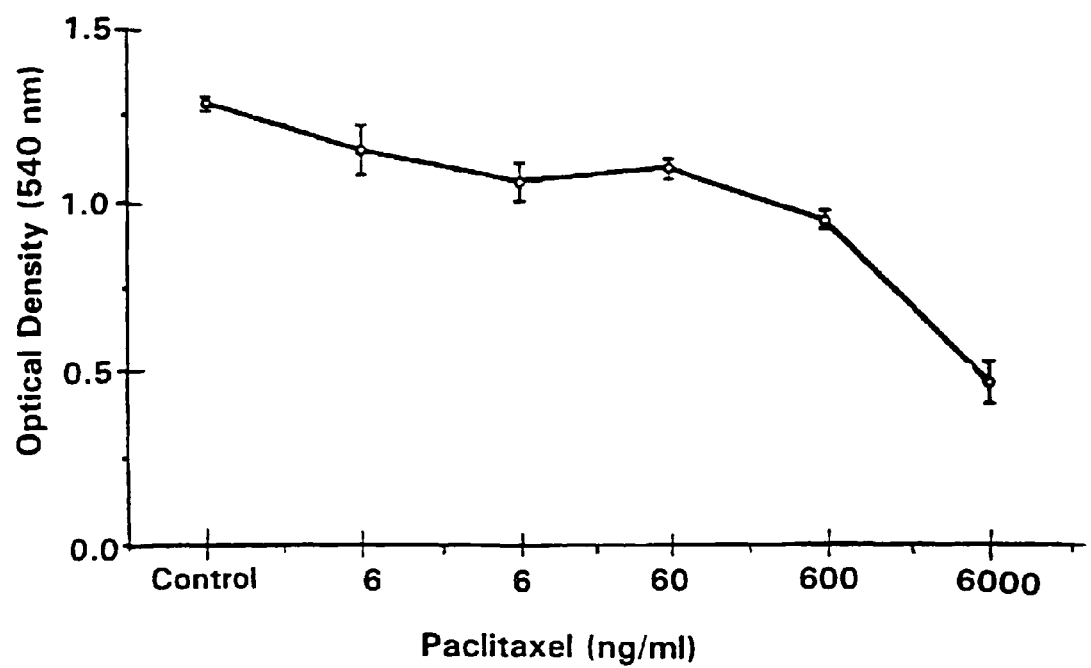
FIGS. 6A-6B. Effect of Paclitaxel (Taxol) and Ceramide on the growth of Tu138 cells. Tu138 cells ($2\times10^4$/well) were plated in 96-well culture plates in the presence and absence of paclitaxel (Taxol) or ceramide for a period of 3 days and then subjected to MTT dye assay as indicated in Materials and Methods. The x-axis represents concentrations of paclitaxel (Taxol) (0-6000 ng/ml.
Figure 6B:
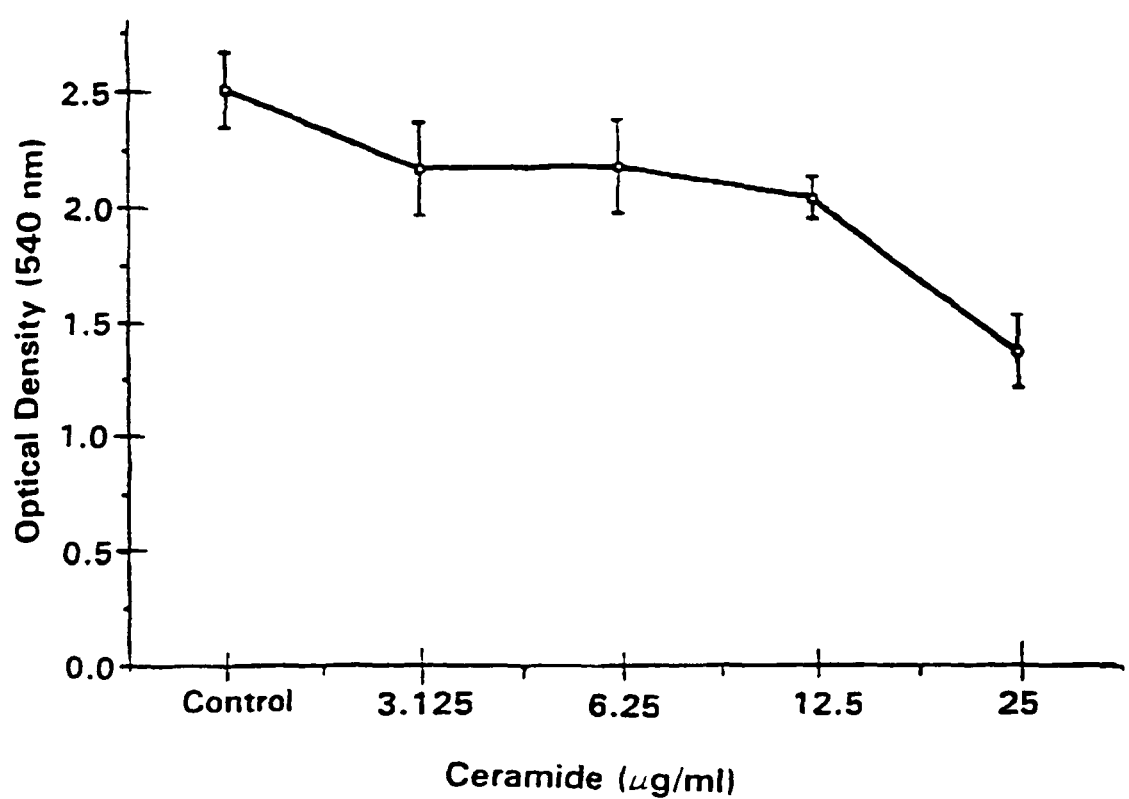

The first set of experiments was directed to observe the cytotoxic effects of paclitaxel and ceramide at different concentrations separately on Tu138 cell line, as measured by MTT dye assay. As shown in FIG. 6A, paclitaxel (Taxol) induced cytotoxicity was observed to be 37% and 64% at 600 and 6000 ng/ml respectively whereas ceramide induced cell effects after 3 days of culture resulted in 19% and 46% cytotoxicity at 12.5 and 25 µg/ml concentrations respectively (FIG. 6B). Multiple repeats (n=6) of these experiments indicated paclitaxel and ceramide induced $ED_{50}$ at concentrations of $1920\pm1200$ ng/ml and $22\pm5$ µg/ml respectively.

Figure 7:
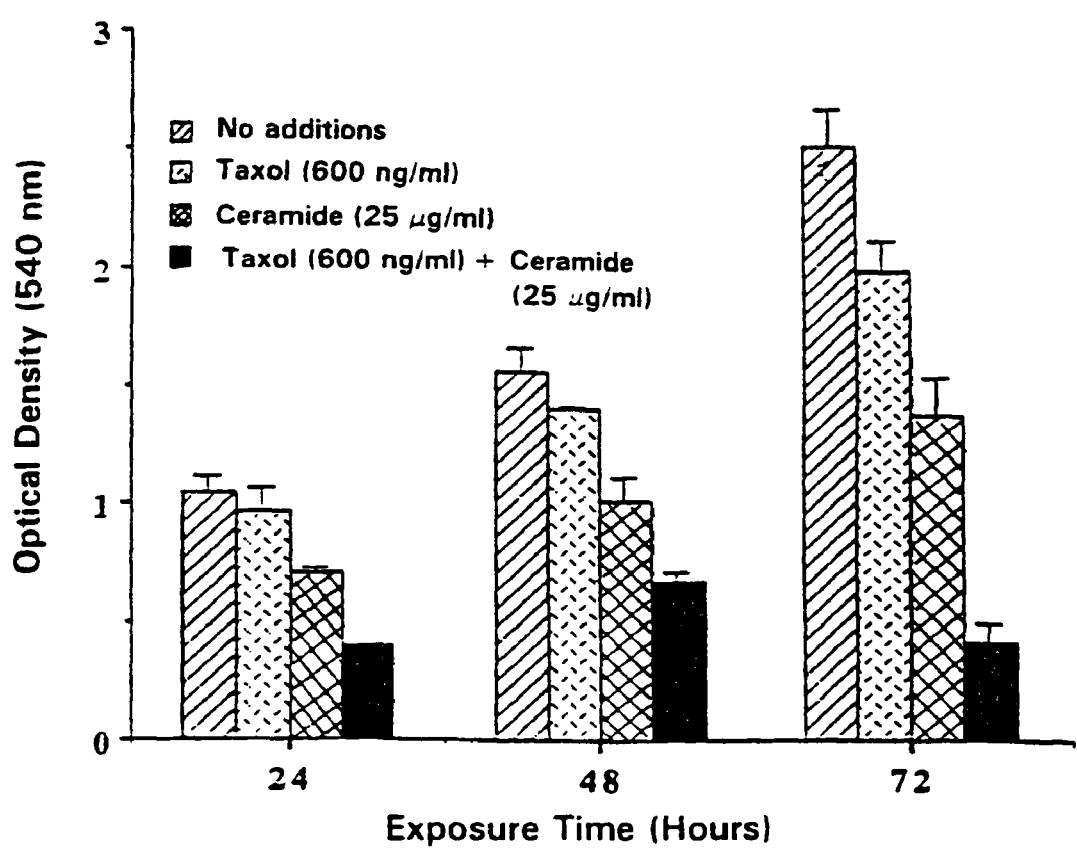
FIG. 7. Time Kinetics of the Combined Action of Paclitaxel (Taxol) and Ceramide. Tu138 cells were cultured as indicated in the FIG. 6 legend in the presence and absence of paclitaxel (Taxol) (600 ng/ml) and/or ceramide (25 µg/ml). The x-axis represents optical density of incorporated dye and y-axis represents the time of measurements at 24, 48 and 72 hours.

To evaluate whether the paclitaxel and ceramide combination enhances cellular cytotoxicity caused by either alone, Tu138 cells were incubated with and without paclitaxel (600 ng/ml) and ceramide (25 µg/ml) simultaneously and separately as control. Cell viability was estimated using the MTT dye assay as a function of time every 24 hours over a period of 3 days. As shown in FIG. 7, paclitaxel (Taxol) when added alone at a concentration of 600 ng/ml indicated cell cytotoxicity from 0.9% at 24 hours to a total of 21.8% by 72 hours. Ceramide also showed an increase in cytotoxicity from 32.7% at 24 hours to 54.5% at 72 hours. The combination of paclitaxel (600 ng/ml) and ceramide (25 µg/ml) treatment showed an increase of approximately 68% in cell cytotoxicity over ceramide alone in a 3 day incubation period. The enhancement of cellular cytotoxicity was also evident in combination treatment at 24 (62.0% cell kill) hours with a maximum cell kill observed at 72 hours. From these results, the combination of both agents seems to indicate an enhancement over an additive effect with respect to a loss of electron transport and subsequent cell viability.

The results of 23 different observations of paclitaxel (600 ng/ml), ceramide (25 µg/ml) and paclitaxel (600 ng/ml) plus ceramide (25 µg/ml) combinations were then subjected to statistical analysis. The mean observed optical density (obtained after different exposures) and the standard deviation were analyzed over the confidence interval with 95% probability. The value of confidence range was compared by assuming a "Student t" distribution in the selected exposure conditions. The paired t-test for (n−1) degrees of freedom demonstrated that the results of paclitaxel and ceramide combination were significantly different with >95% probability than either paclitaxel or ceramide alone.

Synergistic Interaction Analysis by Isobologram

Figure 8:
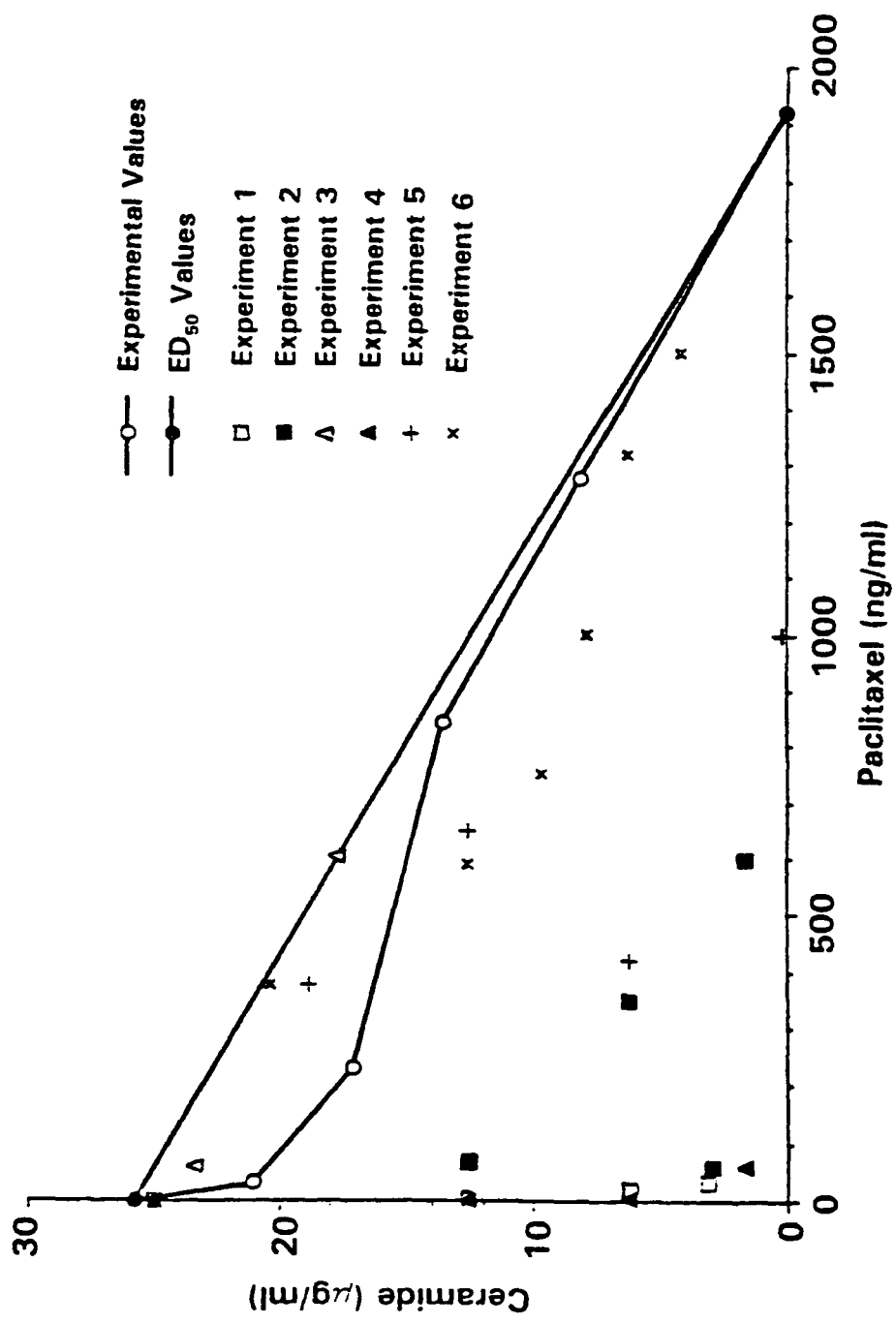
FIG. 8. $ED_{50}$ Isobologram Analysis of Synergistic Action of Paclitaxel (Taxol) and Ceramide. For the construction of isobologram, $ED_{50}$ were determined individually from seven independent experiments performed at various dilutions of paclitaxel and ceramide by best fit analysis. Also, a line plot was generated by calculations of $ED_{10}$ through $ED_{50}$ values for both paclitaxel and ceramide. The x-axis represents paclitaxel (Taxol) concentrations necessary to generate $ED_{50}$ in combination with ceramide concentrations plotted on the y-axis. The scatter plot is the result of calculated $ED_{50}$ values from seven independent experiments representing combined exposures of paclitaxel and ceramide.

To confirm whether paclitaxel and ceramide interactions on Tu138 cell cytotoxicity was synergistic or additive a quantitative isobologram analysis (23, 24) of six independent experiments in triplicates was performed at various dilutions of paclitaxel (0-6000 ng/ml) and ceramide (0-25 µg/ml) separately and simultaneously. A straight line joining points on x- and y-axes (FIG. 8) represents $ED_{50}$ concentrations of paclitaxel (Taxol) and ceramide as determined from six independent experiments. Because of the non-linearity of the dose response curves with either paclitaxel or ceramide alone, a second line plot was generated by calculating $ED_{10}$ through $ED_{50}$ for either agent alone. The line plot represents $ED_{40}$ for paclitaxel combined with $ED_{10}$ of ceramide or paclitaxel $ED_{30}$ plus Ceramide $ED_{20}$ and so on. FIG. 8 represents the isobologram using both the straight line approximation and curve generated from the experimental data to compare the effect of combined additions on synergy. The points to the left of the two line plots that fall within $ED_{50}$ concentrations indicate supra-additive properties of two agents tested in combination. The isobologram analysis indicated that six experiments represented as scatter plots are supra additive. The linear approximation consideration indicated 21 out of 23 experimental points to be synergistic. The experimental determination showed 18 of 23 points in the synergistic range.

Paclitaxel and Ceramide Effects on Cell Cycle Distributions

Figure 9A:
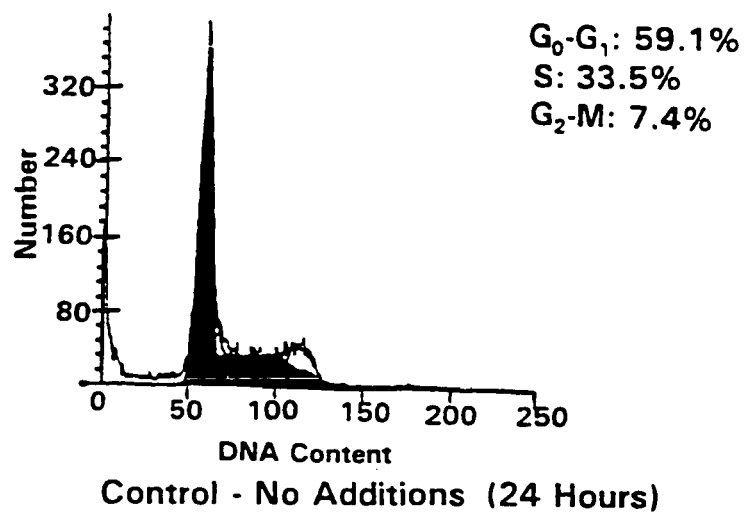
FIGS. 9A-9H: Paclitaxel (Taxol) and Ceramide Induced Cell Cycle Progression and Flow Cytometry Analysis of Tu138 cells. Tu138 cells at a density of $0.5\times10^6$/ml were cultured in the presence and absence of paclitaxel (Taxol) (600 ng/ml) and/or ceramide (25 µg/ml) for 24 (FIGS. 9A-9D panel A) and 48 (FIGS. 9E-9H) hours in either 6-well culture plates to T-25 flasks. At the end of the incubation period, cells were trypsinized, washed and subjected to a flow cytometric analysis as described in Materials and Methods. The x-axis of the scans represents DNA content and y-axis represents the number of cells. The analysis of the acquired samples with the use of "Modfit" software is shown underneath each treatment as the percent population of viable cells in various phases of the cell cycle.
Figure 9B:
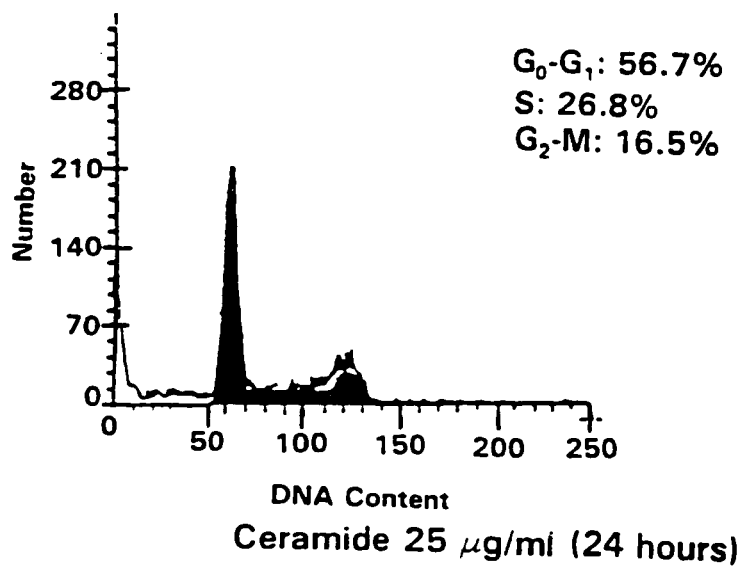
Figure 9C:
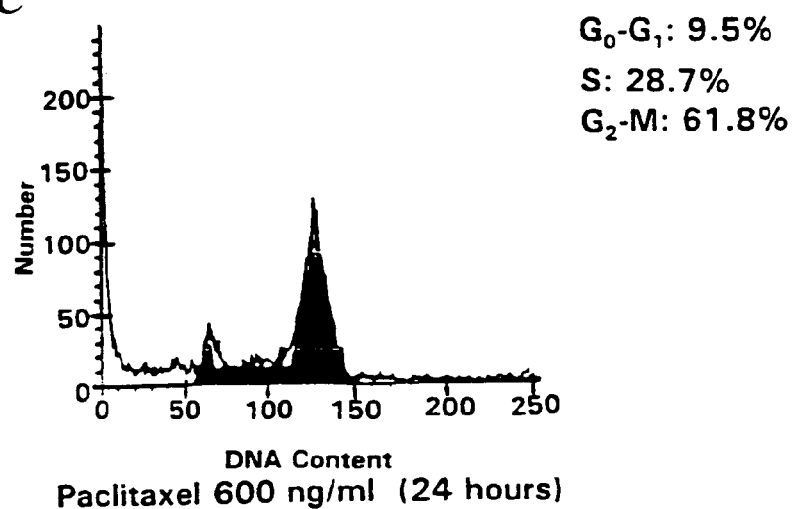
Figure 9D:
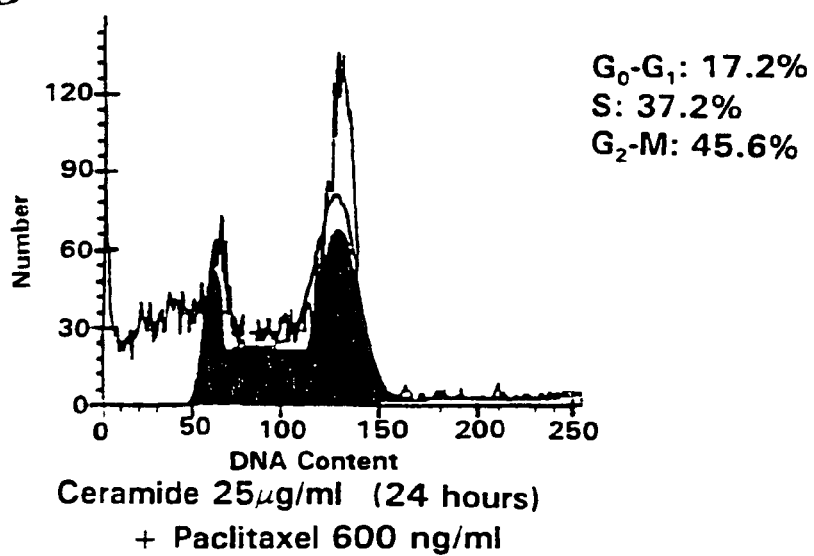
Figure 9E:
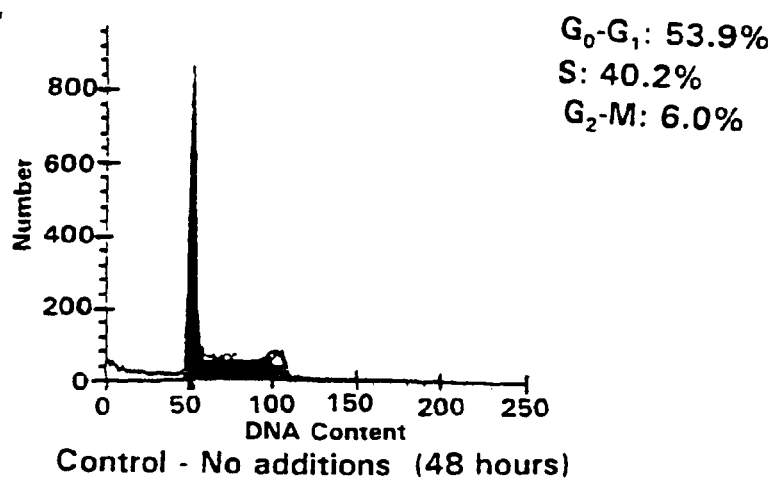
Figure 9F:
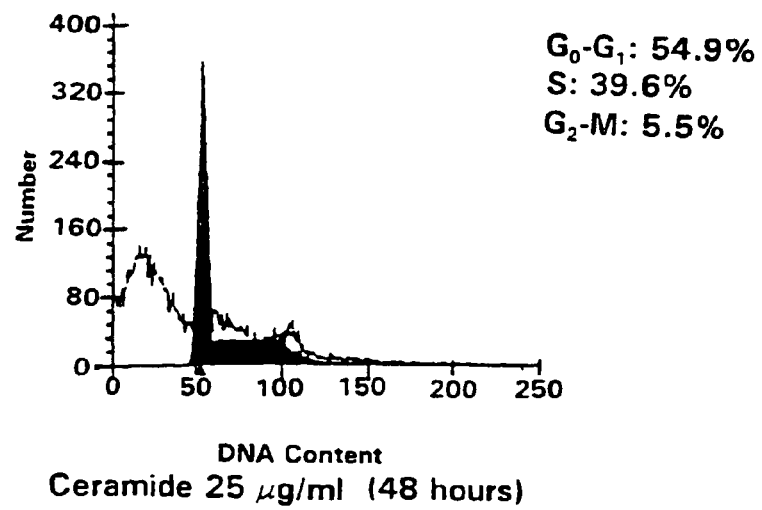
Figure 9G:
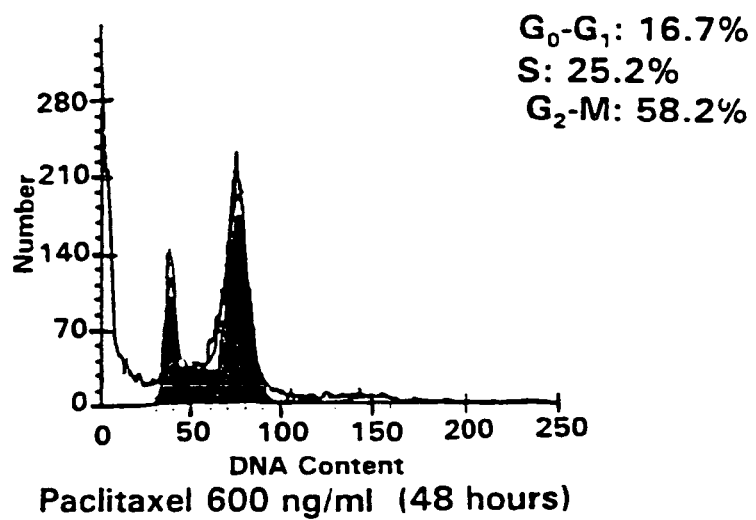
Figure 9H:
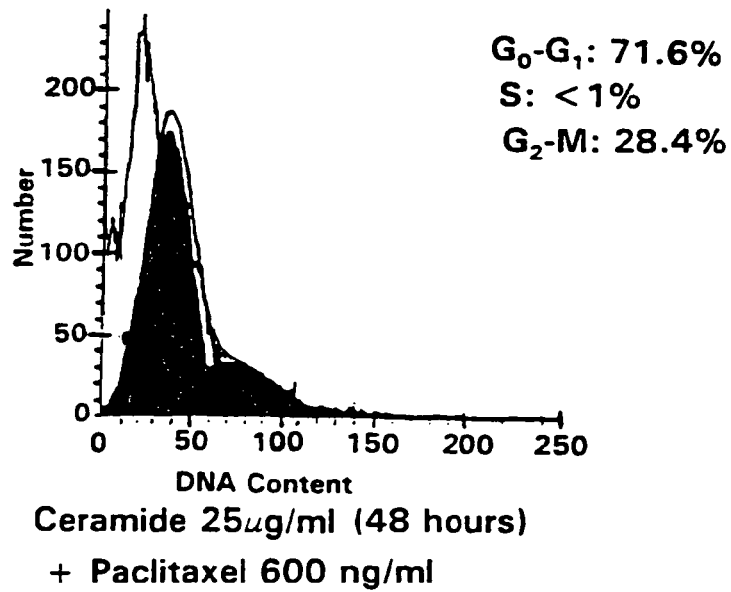

Paclitaxel and ceramide effects have been implicated in cell cycle arrest and apoptosis. To examine whether the interactions of paclitaxel with ceramide would affect the kinetics of cell cycle progression, paclitaxel at 600 ng/ml and ceramide at 25 µg/ml concentrations (at or near $ED_{50}$'s) were utilized to measure the distribution of cells during growth by flow cytometer utilizing propidium iodide staining technique. Since it was difficult to obtain enough viable cells in a sample where combination treatment was utilized after 72 hour exposures, cell cycle measurements were made only at 24 and 48 hours. As FIGS. 9A-9H demonstrate paclitaxel (Taxol) was able to block 61.8% (24 hours) FIGS. 9C and 58.2% FIG. 9G (48 hours) of Tu138 cells in the $G_2$-M phase of the cell cycle in comparison to untreated control cells (7.4% at 24 hours and 6.0% at 48 hours). Ceramide added alone did not significantly affect either $G_0$-$G_1$ or $G_2$-M phase of the cell cycle progression similar to untreated controls (n=4) at either 24 or 48 hours.

In cultures treated simultaneously with paclitaxel (Taxol) and ceramide, a $G_2$-M arrest of 45.6% (FIG. 9D) and 28.4% (FIG. 9H) was observed at both 24 and 48 hours respectively in comparison to paclitaxel (Taxol) treated cultures. This indicated a loss of 26.3% and 51.3% $G_2$-M population of viable Tu138 cells due to the combined effect of paclitaxel and ceramide in comparison to paclitaxel alone at 24 and 48 hours respectively. A significant loss of S-phase population was also observed only at 48 hours. Taken in concurrence with the MTT results, these data indicate cell death occurring either in the $G_2$-M phase or during the exit from the S-phase of the cell cycle.

Induction of Apoptosis by Paclitaxel Paclitaxel and Ceramide Combination

Since the MTT dye assay and the measurement of $G_2$-M cell population cannot determine whether loss of cells is due either to necrosis or apoptosis, and since paclitaxel and ceramide when added alone have been shown to induce apoptosis by several researchers (25, 26), the next series of experiments were directed to examine the mode of cell kill induced by combined exposures of paclitaxel and ceramide at 24 and 48 hours by TUNEL assay. As demonstrated in FIGS. 10A-10H, exposures of paclitaxel (Taxol) (600 ng/ml) and ceramide (25 µg/ml) alone resulted in 18.4% and 9.7% apoptosis at 24 hours respectively whereas both added together induced 53.7% apoptosis indicating an approximately 3-fold increase in comparison to paclitaxel alone. At 48 hours, paclitaxel and ceramide individually induced a 54.8% and 13.6% apoptosis respectively when compared to observed apoptosis of 7.9% in untreated control. When the two agents were added together the percent apoptosis increased to 84.9%. In two separate experiments, paclitaxel and ceramide combinations showed 1.5-fold or greater apoptosis in comparision to paclitaxel alone at 24 and 48 hours.

Discussion

Paclitaxel has clearly been defined as an extremely important new agent in cancer chemotherapy. It has already demonstrated considerable antitumor activities against high staged and relatively resistant tumors of head and neck (18, 27-30). The present studies confirm that paclitaxel is able to arrest the head and neck carcinoma cell line Tu138 in the $G_2$-M phase of the cell cycle. It is also demonstrated that paclitaxel alone is cytotoxic to head and neck carcinoma cells in vitro as demonstrated by the MTT assay ($ED_{50}$: 1920±1200 ng/ml). The large variation in $ED_{50}$ value may be attributed to asynchronous population of Tu138 cells during its growth. Such cell cycle sensitivity and cytotoxicity to paclitaxel has been demonstrated in ovarian, breast, lung and numerous other cell lines (31-34).

Exogenous addition of ceramide has been shown to cause apoptosis in a variety of tumor cell lines (10, 35). In the current studies on solid tumors of head and neck cancer origin, ceramide mediated direct cytotoxicity of Tu138 cell is observed with an $ED_{50}$ of 22±5 µg/ml. In addition, ceramide was shown to induce apoptosis in Tu138 cells as measured by TUNEL assay. However, no significant effect of ceramide on the cell cycle progression of Tu138 cells was demonstrated. This is in contradiction to observed $G_0$-$G_1$ cell block by ceramide in MOLT-4, a leukemic cell line (10).

The combined effect of paclitaxel and ceramide, two drugs with diverse activities, on neoplastic cell cycle progression was examined. It is postulated that if a chemotherapeutic drug such as paclitaxel were to enhance the accumulation of intracellular ceramide which has been suggested to be a mechanism of apoptotic cell death, then the addition of exogeneous ceramide may increase the threshold concentration leading to cellular cytolysis. While data on the necessary and sufficient concentration of intracellular ceramide to induce cytolysis is not available from these results, it is clear that these two agents work synergistically to induce apoptosis. This is confirmed by isobologram analysis demonstrating synergy in >78% of the tested experimental concentrations of paclitaxel and ceramide combined.

These present studies demonstrate that paclitaxel (600 ng/ml) and ceramide, when added separately, are able to kill Tu138 cells via apoptotic mechanisms within 24 hours of exposure. However, when the two agents were combined the observed cytotoxicity was greater than the addition of observed cytotoxicity by paclitaxel and ceramide separately indicating a synergistic interaction between these two agents. In addition, a significant reduction in the cell population in the $G_2$-M phase of the cell cycle within 48 hours due to combined addition of paclitaxel and ceramide was evident from the measurements of cell cycle analysis. Taken together, the MTT dye and TUNEL assay results, seem to suggest that the loss of cell population is from either S or $G_2$-M phase of the cell cycle.

The activation of a number of receptors including TNFα, interferon γ, and Fas signal an intracellular pathway that includes sphingomyelinases which act on membrane sphingomyelin and cause release of the lipid mediator ceramide (36-38). Ceramide may then cause the activation of down stream signal transduction pathways that in turn seem to initiate the final phase of apoptosis involving membrane blebbing, the breakdown of DNA and proteins, fragmentation of organelles, and packaging of cellular debris into apoptotic bodies (12, 39-40). Many chemotherapeutic agents such as doxorubicin have been shown to mediate apoptosis through the involvement of Fas receptor/ligand system (41), which has been questioned in a number of recent studies (42, 43). The engagement of FasR with paclitaxel is yet to be determined. Activation of apoptosis has also been shown to occur directly, through the activation of ceramide synthase with certain chemotherapeutic drugs such as daunorubicin (8). It has been shown that paclitaxel (Taxol) mediates its apoptotic effects via phosphorylation of bcl-2 (15) or the upregulation of BAX (16). Therefore, it is postulated that the mechanism whereby paclitaxel and ceramide mediate a synergistic effect may be via a commonality in downstream signal transduction pathways.

Paclitaxel has been evaluated in combination with cisplatin, doxorubicin and radiotherapy (44-46) in patients with encouraging results. It is important that new combinations be established with better efficacies and be evaluated for patient toxicities. The present results suggest that the addition of ceramide enhances the therapeutic potential of paclitaxel for treatment of head and neck carcinoma.

REFERENCES FOR 3RD SERIES OF EXPERIMENTS

1. Hannun, Y. A. The sphingomyelin cycle and the second messenger function of ceramide. J. Biol. Chem., 269, 3125, 1994.
2. Kolesnick, R. and Golde, D. W. The sphingomyelin pathway in tumor necrosis factor and interleukin-1 signaling. Cell, 77, 325, 1994.
3. Ballou, L. R., Chao, C. P., Holness, M. A., Barker, S. C., and Raghow, R. Interleukin-1-mediated PGE2 production and sphingomyelin metabolism. Evidence for the regulation of cyclooxygenase gene expression by sphingosine and ceramide. J. Biol. Chem., 267, 20044, 1992.
4. Yanaga, F. and Watson, S. P. Ceramide does not mediate the effect of tumour necrosis factor alpha on superoxide generation in human neutrophils. Biochem. J., 298, 733, 1994.
5. Okazaki, T., Bielawska, A., Bell, R. M., and Hannun, Y. A. Role of ceramide as a lipid mediator of 1 alpha, 25-dihydroxyvitamin D3-induced HL-60 cell differentiation. J. Biol. Chem., 265, 15823, 1990.
6. Dobrowsky, R. T., Jenkins, G. M., and Hannun, Y. A. Neurotrophins induce sphingomyelin hydrolisis. Modulation by co-expression of p75NTR with Trk receptors. J. Biol. Chem., 270, 22135, 1995.
7. Venable, M. E., Lee, J. Y., Smyth, M. J., Bielawska, A, Obeid, L. M. Role of ceramide in cellular senecence. J. Biol. Chem., 270, 30701, 1995.
8. Bose, R., Verheji, M., Haimovitz-Friedman, A., Scotto, K., Fuks, Z. and Kolesnick, R. Ceramide synthase mediates daunorubicin-induced apoptosis: and alternative mechanism for generating death signals. Cell, 82: 405-414, 1995.
9. Strum, J. C., Small, G. W., Daiug, S. B. and Daniel, L. W., 1-b-D arabinofuranosylcytosine stimulates ceramide and diglyceride formation in HL-60 cells. J. Biol. Chem., 269, 15493, 1994.

10. Jayadev, S., Liu, B., Bielawska, A. E., Lee, J. Y., Nazaire, F., Pushkareva, M., Obeid, L. M. and Hannun, Y. A. Role for ceramide in cell cycle arrest. J. Biol. Chem., 270, 2047, 1995.
11. Beilawska, A., Linardic, C. M., and Hannun, Y. A. Modulation of cell growth and differentiation by ceramide. FEES Lett, 307, 211, 1992.
12. Obeid, L. M., Hannun, Y. A. Ceramide: a stress signal and mediator of growth supression and apoptosis. J. Cell Biochem., 58, 191, 1995.
13. Jarvis, W. D., Kolesnick, R. N., Formari, F. A., Traylor, R. S., Gewirtz, D. A., and Grant, S. Induction of apoptotic DNA damage and cell death by activation of the sphingomyelin pathway. Proc. Natl. Acad. Sci. USA, 91, 73, 1994.
14. Schiff, P. B., Horwitz, S. B. Taxol stabilizes microtubules in mouse fibroblast cells. Proc. Natl. Acad. Sci. USA, 77, 1561, 1980
15. Haldar, S., Chintapalli, J., and Croce, C. M. Taxol induces bcl-2 phosphorylation and death of prostate cancer cells. Cancer, 56, 1253, 1996.
16. Strobel, T., Swanson, L., Korsmeyer, S., and Cannistra, S. A. BAX enhances paclitaxel induced apoptosis througha p53 independent pathway. Proc. Natl. Acad. Sci. USA, 3, 4096, 1996.
17. Holmes, F. A., Walters, R. S., Theinault, R. L., et al. Phase ll trial of Taxol an active drug in the treatment of metastatic breast cancer. J. Natl. Cancer Inst., 83, 1797, 1991.
18. Forastiere, A. A., and Urba S. C. Simple agents paclitaxel and paclitaxel tifosfamide in the treatment of head and neck cancer. Sem Oncol., 22: 24-27, 1995.
19. Cortes-Funes, H. and Aisner, J. Paclitaxel in head and neck cancer and other tumor types. Sem. Oncol., 24, 52, 1997.
20. Liu T. J., Zhang W. W., Taylor D., Roth J., Goepfert H. and Clayman G. Growth suppression of head and neck cancer cells by the introduction of a wild-type p53 gene via a recombinant adenovirus. Cancer Res., 54, 3662, 1994.
21. Clayman, G., Liu, T, Overholt, M, Mobley, S., Wang, M., Janot, F. and Goepfert, H. Gene therapy for head and neck cancer. Arch Otolaryngol Head Neck Surg, 122, 489, 1996.
22. Carmichael, J., DeGraf, W. J., Gazdar, A. F., Minna, J. D. and Mitchell, J. B. Evaluation of a Tetrazolium-based semiautomated colorimetric assay: assessment of chemosensitivity testing. Cancer Res., 47, 936, 1987.
23. Elion, G B, Singer, S and Hichings G H. Antagonists of nucleic acid derivatives. VIII. Synergism in combinations of biochemically related antimetabolites. J. Biol. Chem., 208, 477, 1954.
24. Chou, T. C. and Talalay P. Quantitative analysis of dose-effect relationships: the combined effect of multiple drugs and enzyme inhibitors. In: Advances in enzyme regulation. G. Weber, ed, Pergamon Press, N.Y., pp 27-55, 1984.
25. Milross, C. G., Mason, K. A., Hunter, N. R., Chung, W, Peters, L. and Milas, L. Relationship of mitotic arrest and apoptosis to antitumor effect of paclitaxel. J. Natl. Cancer Inst., 88, 1308, 1996.
26. Hannun, Y. Functions of ceramide in coordinating cellular responses to stress. Science, 274, 1855, 1996.
27. Forastiere, A. A. Paclitaxel (Taxol) for the treatment of head and neck cancer. Sem in Oncol, 21: 45, 1994.
28. Wanebo, H. J., Chougule, P., Ackerley, W., Konness, R. J., McRae, R., Nigri, P., Leone, L, Safran, H., Webber, B., Cole, B. Preoperative paclitaxel, carboplatin and radiation in advanced head and neck cancer (Stage III and IV) induces high rate of complete pathologic response (CR) at the primary site and high rate of organ preservation. Proc. Am. Soc. Clin. Oncol., 16, p. 391a, 1997.
29. Smith, R. E., Thornton, D. E., and Allen, J. A phase II trial of paclitaxel in squamous cell carcinoma of the head and neck cancer correlative lab studies. Sem. Oncol., 22, 41, 1995.
30. Creaven, P., Rayhavan, C., Pendayala, D. et al. Phase 1 study of paclitaxel and carboplatin: Implications for trials in head and neck cancer. Sem Oncol., 22, 13, 1995.
31. McGuire, W., Rowinsky, E., Rosenshein, N., Grumbine, F., Ettinger, D., Amstrong, D., and Donehower, R. Taxol: A unique antineoplastic agent with significant activity in advanced ovarian epithelial neoplasms. Am. J. Intern. Med., 11, 273, 1989.
32. Rowinsky, E., Donehower, R., Jones, R., and Tucker, R. Microtubule change and cytotoxicityin leukemia cell lines treated with Taxol. Cancer Res., 48: 4093, 1988.
33. Chuang, L., Lotzova, E., Leath, J., Cook, K., Munkanah, A., Morris, M., and Wharton, J. Alterations of lymphocyte microtubule assembly, cytotoxicity and activation by the anticancer drug Taxol. Cancer Res., 54, 1286, 1994.
34. Steren, A., Sevin, B., Perras, J., Angioli, R., Ngugen, H., Guerra, L., et al. Taxol sensitizes human ovarian cancer cells to radiation. Gynecol. Oncol., 48, 252, 1993.
35. Sweeney, E, Sakakura, C., Shirahama, T., Masamune, A., Ohta, H., Hakomori, S, and Igarashi, Y. Sphingosine and its methylated derrivative N,N-dimethyl sphingosine (DMS) induce apoptosis in a variety of human cancer cell lines. Int. J. Cancer, 66, 358, 1996.
36. Dressler, K. A., Mathias, S, and Kolesnick, R. N. Tumor necrosis factor-alpha activates the sphingomyelin signal transduction pathway in a cell-free system. Science, 255, 1715, 1992.
37. Kim, M. Y. Identification of sphingomyelin turnover as an effector mechanism for the action of tumor necrosis factor alpha and gamma-interferon. Specific role in cell differentiation. J. Biol. Chem., 266, 484, 1991.
38. Gulbins, E., Bissonette, R., Mahboudi, A., Martin, S., Nishioka, W., Brunner, T., Baier, G., Baier-Bitterlich G., Lang F. et al. FAS-induced apoptosis is mediated via a ceramide-initiated RAS signaling pathway. Immunity, 2, 341, 1995.
39. Kerr, J. F., Wyllie, A. H., and Currie, A. R. Apoptosis: a basic biological phenomenon with wide ranging implications in tissue kinetics. Br. J. Cancer, 26, 239, 1972.
40. Bursh, W., Kliene, L., and Tenniswood, M. The biochemistry of cell death by apoptosis. Biochem. Cell. Biol., 68, 1071, 1990.
41. Friesen C., Herr, I., Krammer, P H and Debatin K M. Involvement of the CD95 (APO-1/FAS) receptor/ligand system in drug-induced apoptosis in leukemia cells. Nature Medicine, 2, 574, 1996.
42. Villunger, A., Egle, A., Kos, M., Hartmann B L, Geley S, Kofler R and Grell R. Drug-induced apoptosis is associated with enhanced Fas (Apo-1/CD95) ligand expression but occurs independently of Fas (Apo-1/CD95) signaling in human T-acute lymphatic leukemia cells. Cancer Res., 57, 3331, 1997.
43. Eischen, C. M., Kottke, T. J., Martins L M, Basi, G. S., Tung J. S., Earnshaw, W. C., Liebson P J and Kaufmann S H. Comparison of apoptosis in wild-type and Fas-resistant cells: chemotherapy-induced apoptosis is not dependent on Fas/Fas ligand interactions. Blood, 90, 935-43, 1997.
44. Fountzilas G., Athanssiadis, A., Samantas, E. et al. Paclitaxel and carboplatin in recurrent and metastatic head and neck cancer: A phase II study. Semin. Oncol. 24, S265-S267, 1997.

45. Hitt, R., Hornedo, J., Colomer, R., et al. Study of escalating doses of paclitaxel plus cisplatin in patients with inoperable head and neck cancer. Semin. Oncol. 24, S258-S264, 1997.
46. Conley, B., Jacobs, M., Suntharalingam et al., A pilot trial of paclitaxel, carboplatin and concurrent radiotherapy for unresectable squamous cell carcinoma of the head and neck. Semin. Oncol. 24, S278-S280, 1997.

4th Series of Experiments

In Vivo Studies Tu135 Cells

Ceramide, a sphingomyelin metabolite, provides the "death signal" for apoptosis in mammalian cells. Paclitaxel, an active chemotherapeutic agent, blocks cells in the G2/M phase of the cell cycle. It has been shown that paclitaxel and ceramide have synergistic cytotoxic effects on the leukemic T-cell line Jurkat (D. Myrick, 1999, in press). The interaction of paclitaxel and ceramide in a variety of solid tumor cancer cell lines is further explored herein to determine whether there is similar synergism in inducing cytotoxicity and apoptosis.

Materials and Methods

Neoplastic human cell lines included Prostate (LnCaP), Colon (HT29), Pancreatic Cancer (RWP-2) and head and neck squamous carcinoma (TU138) which were maintained in RPMI-1640 containing 10% fetal bovine serum. C6-Ceramide (Sigma Chemicals) initially dissolved in ethanol and paclitaxel (Taxol) (Bristol-Myers, Squibb, Inc.) were diluted in RPMI. Each neoplastic cell line at $25 \times 10^3$ was incubated at 37° C. in the presence and absence of Paclitaxel with varying concentrations of Ceramide and were subjected to the MTT dye assay for surviving cell fractions at 72 hrs.

In Vivo Studies

TU138 cells were implanted subcutaneously in nude mice Balb/c NU/NU which were treated beginning on day 4 with thrice weekly injections of Paclitaxel 120 μg/0.1 ml, Ceramide, 500 μg in 0.2 ml, or the combination and control vehicle, and were observed over 6 weeks.

Results

Paclitaxel induced cytotoxicity in most tumor cell lines tested with an ID50 of 6.0-60.0 ng/ml. Ceramide was equally cytotoxic at calculated ID50 of approximately 30.0-40.0 μg/ml. Combination of the two enhanced cellular cytotoxicity in a synergistic manner (as indicated by the 50% isobologram).

TABLE 2

% Growth Inhibition of Human Cancer Cell Lines by Paclitaxel (Taxol) and Ceramide Alone and in Combination

| CELL LINE | PACLITAXEL (600 ng/ml) | CERAMIDE (25 μg/nl) | PACLITAXEL (600 ng/ml) plus CERAMIDE (25 μg/ml) |
| --- | --- | --- | --- |
| HT29 | 16% | 61% | 81% |
| Jurkat | 55% | 8% | 78% |
| LnCap | 13% | 25% | 66% |
| PC-3 | 16% | 8% | 51% |
| RWP-2 | 2% | 6% | 75% |
| TU138 | 10% | 28% | 66% |

Figure 11:
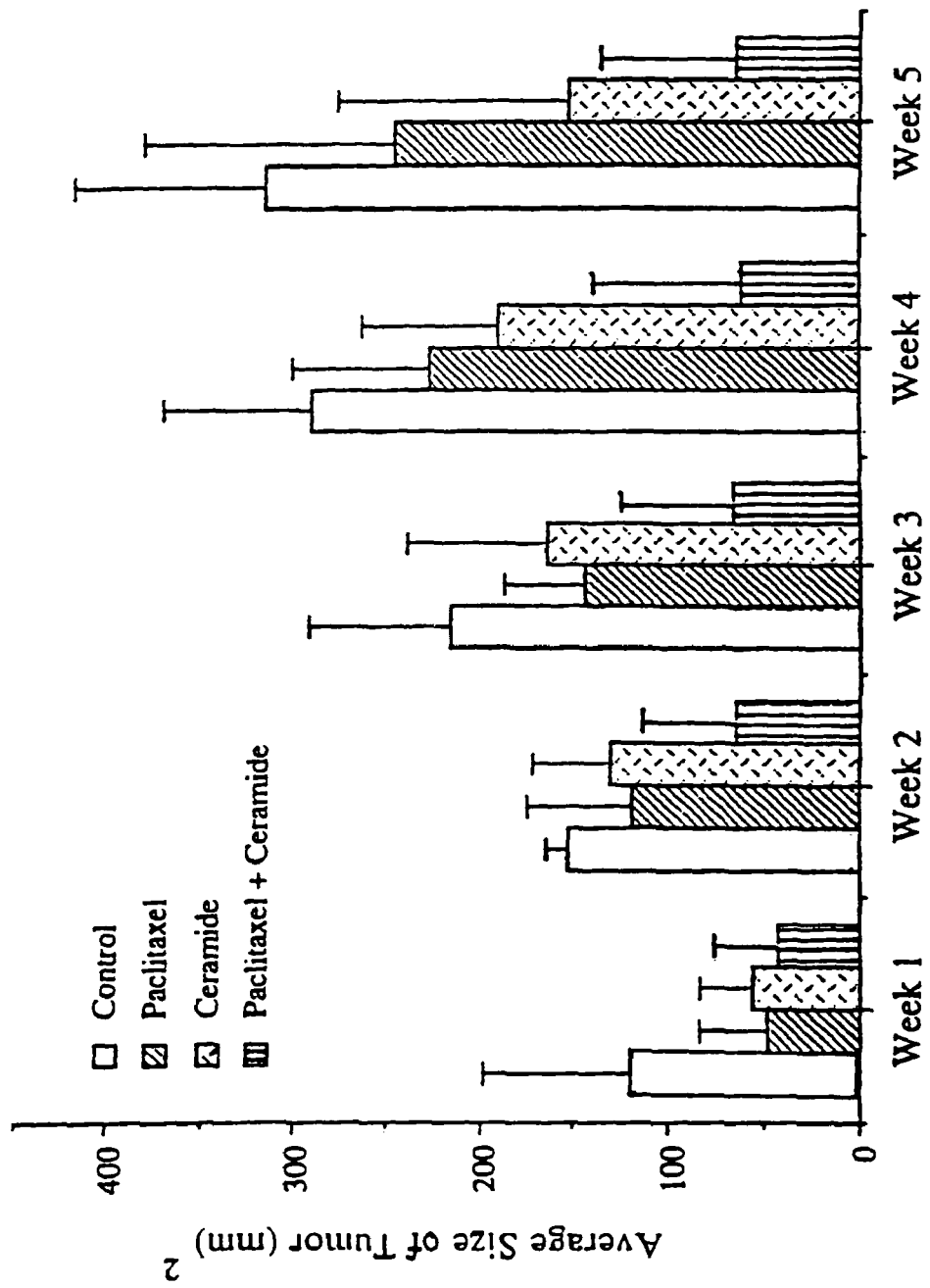
FIG. 11. Growth of Human Squamous Carcinoma Cells in Nude Mice. Tumor growth of head and neck squamous carcinoma (TU138) was significantly reduced by treatment with a combination of paclitaxel and ceramide.
Figure 12:
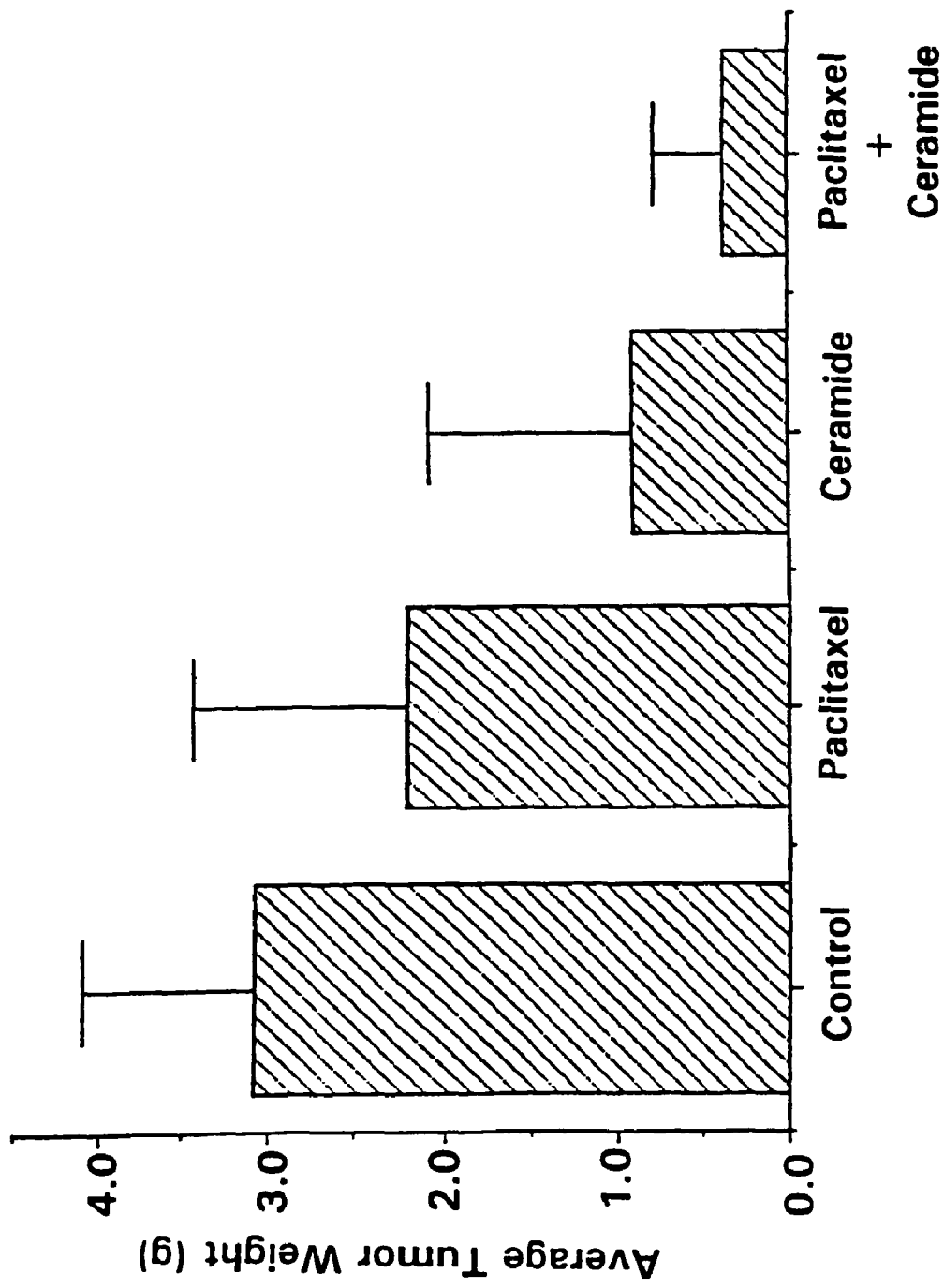
FIG. 12. Excised Tumor Weights in Nude Mice. Tumor growth of head and neck squamous carcinoma (TU138) was significantly reduced by treatment with a combination of paclitaxel and ceramide compared with tumor growth reduction in control, nude mice treated with paclitaxel alone, and nude mice treated with ceramide alone.

Tumor growth of TU138 was significantly inhibited by combination of Paclitaxel and Ceramide (FIGS. 11 & 12)

Discussion

Ceramide enhances Paclitaxel-mediated cytotoxicity in several tumor cell lines and augments the anti-tumor effect of paclitaxel on one of the lines (TU 138) in an in vivo nude mouse model. The mechanism is not yet defined but in part appears related to cell cycle switching by Paclitaxel (G2/M cell cycle block) although other considerations related to apoptosis are under study (bcl-2 and BAX system, changes in intracellular ceramide and Fas ligand mediated events.

5th Series of Experiments

Treatment of Breast Cancer with Chemotherapeutic Agents and Ceramide

Cancer of the breast continues to be the most common cause of death in middle aged women. Both its annual incidence and mortality in western countries are on the increase and the majority of women who develop breast cancer ultimately die of recurrent or metastatic disease. It is important to utilize new drugs in maximally efficient therapeutic strategies to slow or eliminate the disease progression. This invention provides an innovative and explorative method of treatment using the lethal combination of diverse agents, paclitaxel and a naturally occurring ceramide. This invention concurrently provides the therapeutic basis of paclitaxel action on breast tumor cell in vitro leading to better and less toxic therapeutic strategies. The explorative method has evolved from different experimental protocols. Specific aims of the present study include demonstrating most effective conditions of paclitaxel and of ceramide (a) to affect growth arrest leading to subsequent synergistic cytotoxic effects in combined protocols; (b) to establish if liposome formulation can enhance the synergistic action of both agents. It will also establish if both agents can be formulated together in liposome to enhance their effects.

Cancer of the breast continues to be the most common cause of death in middle aged women. Both its annual incidence and mortality in western countries are on the increase and the majority of women who develop breast cancer ultimately die of recurrent or metastatic disease. Despite a considerable research effort and controlled clinical trials, the management of breast carcinoma is as confused and shows partial success until drug resistant tumors begin to grow. It is important to utilize new drugs in maximally efficient therapeutic strategies to slow or eliminate the disease progression.

This innovative and explorative study uses the most lethal combination of two diverse agents, paclitaxel and a naturally occurring compound termed ceramide. Concurrently, the in vivo application of these two agents in an animal model utilizing human breast carcinoma cells is examined. This explorative method has evolved from the application of these two agents first, in in vitro studies of a variety of neoplastic cell lines including leukemic, prostate, pancreatic and squamous cell carcinoma and second, in an in vivo study of a squamous carcinoma cell line in nude mice.

These preliminary studies have shown that the combination of paclitaxel and ceramide given at the time of the initiation of cultures in vitro induces apoptosis in a variety of cell lines synergistically as measured by either flow cytometry, Wright cell analysis or by a TUNEL assay. The synergistic interaction was also confirmed by isobologram analysis. These studies also demonstrated that the apoptotic cells were derived from either S or the $G_2$-M phase of the cell cycle. The studies on the mechanisms of action of these agents when added separately have identified few common pathways leading to apoptosis. It is hypothesized that paclitaxel or cermide exposures will lower the required threshold of each agent, thereby reducing patient toxicity.

Just as combination chemotherapy is superior to single agent chemotherapy in advanced disease, it is plausible that better drug combinations will lead to improved adjuvant therapy results. Improved understanding of drug-cell interactions will not only expand present knowledge of therapy but also provide some indication of the design for future trials.

Although significant progress has been made in the management of breast carcinoma, improved treatment strategies are urgently needed for both locally advanced and metastatic breast carcinoma. Paclitaxel is a new agent with important cytotoxic activity in a variety of tumor cells and has demonstrated radiation sensitizing ability in select tumor cell models. The role of paclitaxel in the treatment of breast carcinoma is beginning to be established although its cellular mechanisms of action are still being defined. It is critical, however, to design adjuvant, neo adjuvant therapy for the treatment of recurrent disease.

Tumor Cell Growth and Drug Selection

The most important feature of malignancies is the clonal origin of tumor cells and their retention of proliferative capacity (1). The principle of therapy with cytotoxic drugs relies on the selective inhibition/lysis of neoplastic cells and not the normal cells or tissues. The basis for most chemotherapeutic drug action is the inhibition of DNA, RNA and/or protein synthesis. Since the growth of tumors is usually described by Gompertzian kinetics (2, 3), the effectiveness of chemotherapeutic drugs is determined by tumor growth fraction, doubling time and size. Furthermore, the application of chemotherapy, as outlined by the Goldie-Coldman (4) model, suggests that cells will mutate to develop drug resistance based on the inverse relationship between cure and cell number and is independent of the neoplastic cell growth kinetics. This model provides the basis for (a) early initiation of treatment when tumor burden or fraction and the likelihood of drug resistance is small and (b) effective treatment utilizing a combination of drugs to lower side effects and toxicities to achieve maximal neoplastic cell kill.

The specific drug selection in a given protocol is usually based on the mechanism of action of the drug in question, its effects on the cell cycle, its toxicity and its effectiveness against a given tumor. Paclitaxel (Taxol) is another antineoplastic agent isolated from the *Taxus brevifolia*, more commonly known as the Western Yew (5). The proposed mechanism whereby paclitaxel induces cytotoxicity is the stabilization of polymerization of tubulin monomers and prevention of depolymerization. This leads to the arrest of the paclitaxel responsive cells in the $G_2$-M phase of the cell cycle. In contrast to Vincristine which affects the assembly of microtubules, paclitaxel blocks the depolymerization of assembled microtubules (6), thereby causing arrest of growing cells in the mitotic phase of the cell cycle. The formation of multidrug resistant phenotype with the overproduction of P-glycoprotein has been shown to be a consequence of paclitaxel exposure (7) suggesting the need for developing treatment strategies which minimize the development of resistance. Although a variety of research projects and clinical trials have recently sought to determine the antineoplastic action of paclitaxel in relation to breast carcinomas, its direct cellular (cell cycle progression) and molecular effects are only beginning to be elucidated.

Breast Cancer: Paclitaxel in Clinical Therapy

Paclitaxel as a single agent (n=25, 250 mg/m$^2$, 24 hour infusion every 21 day interval) has been evaluated in clinical trials of recurrent breast cancer with a complete and partial response rates of 12% and 44% respectively (8). The dose related toxicity, however, was severe. Interestingly, in a therapeutic regimen of paclitaxel with doxorubincin it was observed that patients had impairment in the elimination of doxorubicin if paclitaxel was administered first suggesting a need for drug sequencing studies in a combination protocol.

In Eastern Cooperative Oncology Group (ECOG) studies (9) the maximally tolerated doses of doxorubicin (60 mg/m$^2$) and paclitaxel (175 mg/m$^2$) are given as a 24 hour continuous infusion in different combinations over a period of 3 weeks. In a separate study of chemotherapy-naive metastatic breast cancer, a 3 hour infusion of paclitaxel (90 mg/m$^2$) is followed by a 60 mg/m$^2$ cisplatin every 2 weeks (10). This protocol allows for an increase in the dose of paclitaxel up to 130 mg/m$^2$ without changing the cisplatin dose. While severe toxicity is observed, the results of this study demonstrate 25% complete and 69% partial response rates with an overall response rate of 94%. In another combination therapeutic protocol for recurrent breast carcinoma (n=40), paclitaxel (135 mg/m$^2$) has been administered with cyclophosphamide (750 mg/m$^2$) in various combinations with the following results (11): partial response: 4, no change: 18 and progressive disease: 18. While the efficacy of paclitaxel as a single agent is yet to be established, its combination with different agents has shown promising results in selected patients.

Breast Cancer: In Vitro and In Vivo Animal Studies with Paclitaxel

Many in vitro cellular studies and in vivo animal studies with human breast carcinoma cells have sought to examine the effect of various cytotoxic agents with paclitaxel. These cytotoxic agents include etoposide, vinorelbine, cis-platin, vinblastin and tamoxifen. The studies with etoposide in combination with paclitaxel demonstrated optimal effect on MCF-7, a breast carcinoma cell line to be dependent on the delivery schedule of the drugs in a sequential manner (12). Paclitaxel induced growth inhibition of MCF-7 in the presence of cis-platin demonstrated merely additive effects (13). Interestingly, while both vinorelbine and paclitaxel bind to distinct sites on tubulin with opposing effects on microtubules they demonstrated synergistic effects on MCF-7 cell cytotoxicity when administered concurrently. Paclitaxel has been demonstrated to be efficacious on hormone refractory breast cancer cells (14), tumor cells with disruptions in p53 (15) or cells with overexpression of HER-2 gene (16).

Additionally, many recent studies have examined (a) the differential effects of drugs or agents on cell cycle progressions. In these studies, panel of cells including breast carcinoma were combined with adenovirus-mediated gene therapy ($G_0$-$G_1$ blocker) in combination with either simultaneous or post paclitaxel ($G_2$-M blocker) treatment (17). While no interactive antagonistic activity was observed, the combination had either synergistic or additive effect. Interestingly, the relative concentration of each agent determined the dominant response in terms of cell cycle progression and cell death; (b) the activation of molecular pathways leading to apoptosis with the help of radioimmunotherapy. These studies demonstrated that timing and sequencing of paclitaxel and 90Y-DOTA-peptide-ChL6 antibody (90Y-ChL6) is critical in combined modality for maximal effectiveness in human breast carcinoma cells (HBT 3477) in nude mice (18); and (c) the inhibition of angiogenesis by paclitaxel in addition to Vincristin, colchicin and 2-methoxyestradiol (19).

It is clear the review of literature on paclitaxel presented here indicates the following: (a) paclitaxel in combination with other drugs is more effective than as a single agent, (b) the definition of the mode of addition of different agents in a combination protocol is essential to achieve maximum therapeutic benefit, (c) the mechanism of action for the induction of apoptosis may be dependent on the concentration of available paclitaxel and (d) the sequential addition of low dose over an extended period of time may be more effective than one big bolus of paclitaxel. These studies also suggest that the discovery of a new agent, ceramide, that complements and amplifies the action of paclitaxel is important consideration in therapeutic strategies to eventually eliminate the abnormal growth of tumor cells.

Ceramide and Breast Cancer

Sphingolipods have been shown to be biologically active and have numerous regulatory effects on cell function including cell growth and differentiation. A number of inducers of sphingomyelin hydrolysis causing concommittant elevation of intracellular ceramide have been identified. These include TNFα, endotoxins, interferon alpha, IL-1, Fas ligand, chemotherapeutic agents, heat and ionizing radiation (20). Ceramide synthesis de novo has been implicated in lethal responses to several chemotherapeutic agents such as anthracyclins (21) and ara-C (22). Many recent studies have examined the effect of exogeneous ceramide on the induction of apoptosis in a variety of tumor cells. Ceramide has been shown in such cases to cause cell cycle arrest in several cell lines as well as apoptosis, cell senescence and terminal differentiation (23-26). The role of ceramide induced cytotoxicity in breast carcinoma is reported by many laboratories. These studies have examined the effect of cell permeable C6-ceramide to cause apoptosis in TNFα resistant MCF-7 cell line and increase in intracellular ceramide as a consequence of sphingomyelin hydrolysis due to the addition of TNFα on sensitive MCF-7 cells (27). Cell permeable C2-ceramide was shown to cause apoptosis in another human breast cancer cell line, Hs578T which was enhanced by the addition of insulin-like growth factor binding protein-3 (28). Interestingly, suramin-induced cell death in human breast, prostate and neuron like cell lines have been shown to have elevated levels of intracellular ceramide prior to apoptosis (29).

Mechanisms of Action in Paclitaxel or Ceramide Induced Apoptosis

There are many proposed mechanisms of action for paclitaxel induced cell death. These include the phosphorylation of bcl-2 (30) in prostate cancer cells, transient activation of JNK pathway (31) in leukemic cells and sensitization and activation of FasR on cell surface (1st series of experiments). Similarly, multitudes of apoptotic pathways leading to the activation of bcl-2/BAX, JNK/SAPK, FasR/FasL, etc. have been proposed as a consequence to ceramide addition in a variety of cellular models (32). It should be pointed out that no studies have recorded the combined effects of paclitaxel and ceramide on many of these proposed pathways.

Preliminary Studies: Paclitaxel and Ceramide Action In Vitro

The present studies (1st series of experiments) with a human leukemic T-cell line, Jurkat have demonstrated that the addition of C6-ceramide enhanced paclitaxel-mediated apoptosis in a synergistic manner. These studies also established that the apoptotic population of Jurkat cells was from either S or $G_2$-M phase of the cell cycle. In these studies, the apoptosis was measured by Wright stain, TUNEL assay and flow cytometric evaluations.

Paclitaxel and cell permeable C6-ceramide mediated synergy for observed apoptosis was also evident in a squamous carcinoma cell line, TU-138. The evaluation of apoptosis was carried out by TUNEL assay. Flow cytometric studies confirmed the earlier observations with Jurkat cells that the loss of cells to apoptosis was derived from either S or $G_2$-M phase of the cell cycle. The synergistic response of paclitaxel and ceramide was confirmed by the isobologram analysis and its significance was established by student's T-test.

It was also observed that paclitaxel and C6-ceramide induced synergistic growth inhibition in a variety of tumor cell lines including prostate (hormone sensitive LnCaP and hormone refractory PC-3), pancreatic (RWP-2) and breast (MCF-7) carcinoma cell lines.

In addition, the studies with breast carcinoma cell line, MCF-7 have suggested that the concentration of paclitaxel added at the onset of cultures is critical to the progression of cell cycle. At lower than $ID_{50}$ paclitaxel concentrations (0.6-6.0 ng/ml), it was more efficacious, blocking greater than 55% of cells in to $G_2$/M phase of the cell cycle. Interestingly, at higher than $ID_{50}$ concentrations, paclitaxel clearly affected the movement of cells from $G_1$ phase of the cell cycle reducing the number of cells into $G_2$/M phase to 38%.

Preliminary Studies: Paclitaxel and Ceramide Action In Vivo

To corroborate the in vitro findings of synergistic action of paclitaxel and ceramide, TU-138 cells were planted subcutaneously in nude mice at day 0. The treatment with paclitaxel (120 μg in 0.1 mL) and ceramide (500 μg in 0.2 mL) was begun on day 4 with thrice weekly injections administered subcutaneously near the site of the tumor implantation on squamous cell carcinoma cell line TU-138 for a period of 5 weeks. The following control groups were run: vehicle only, paclitaxel alone and ceramide alone. The size of the tumor was measured once a week and continued for 6 weeks (FIG. 11). All groups of mice were sacrificed on day 45 and the excised tumor was weighed (FIG. 12). The data presented are preliminary, but nevertheless indicate that TU-138 cell-tumor grew aggressively in control and paclitaxel treated mice almost equally. The group with only ceramide injections demonstrate a slight decrease in tumor size at week 5. The group with both paclitaxel and ceramide showed a decline of 79% in tumor size in comparison to control group.

The significant reduction (88% in paclitaxel+ceramide in contrast to control only) in tumor weight corraborated these findings as shown in FIG. 12. Interestingly, the ceramide only group did demonstrate a substantial reduction in tumor weight. The data is currently being evaluated statistically. The excised tumors are currently being subjected for histopathological studies to determine tumor cell morphology and cellular apoptosis.

The existing protocols of combination chemotherapy utilizing paclitaxel are only partially effective. Therapeutic strategies that involve ceramide in vivo in breast carcinoma have not been reported yet.

Paclitaxel induces transient growth arrest of breast cancer cells into the G2-M phase of the cell cycle. A simultaneous or progressive addition of ceramide, a $G_0$-$G_1$ blocker, will result in greater apoptosis either by targeting those cells that escaped paclitaxel effects or by activating complementary apoptotic pathways. This will result in increased effects of paclitaxel at concentrations lower than those currently employed in clinical protocols.

Technical Objectives

The long-term objectives of this study include determination of the most efficacious clinical and therapeutic basis of paclitaxel effects on breast cancer cells. These studies focus on (a) examinations of the kinetics of the combined effects of paclitaxel and ceramide in cell growth inhibition and lysis in vitro and (b) corraboration of the in vitro studies in an in vivo nude mouse model utilizing breast carcinoma cell line. The specific aims of the studies are set forth below.

Evaluation of paclitaxel and ceramide in a combination therapy utilizing a nude mouse model bearing human breast tumor: Paclitaxel as a single agent has been shown to negatively modulate the growth of breast carcinoma in the clinic and also in the laboratory studies. Cell-permeable exogeneously added ceramide has also been shown to induce apoptosis in a variety of cancer cell lines in vitro including breast carcinoma. The studies combine these two agents with diverse mechanism of actions to enhance the cytotoxic effects of each other. This innovative approach is based on the rationale that unaffected cells by one agent will be targeted by the other agent as a direct effect. At the same time these two agents will amplify the converging point(s) in an otherwise enhanced pathway toward apoptosis resulting in a synergistic interaction. Such synergistic action has been observed with paclitaxel and ceramide in a squamous carcinoma cells grown in vivo in nude mice in the laboratory.

Establish the necessary and sufficient conditions for the growth inhibition and cellular cytotoxicity effects of paclitaxel and ceramide when added simultaneously or in sequence followed by the determination of apoptosis of the cells of breast carcinoma: The studies focus on the kinetics of the addition of paclitaxel and/or ceramide and their effect on cell cycle progression of breast cancer cells. The studies also investigate apoptosis by a variety of available methods.

Experimental Design and Methods:

Breast Cancer and Drug Delivery

Combination drug delivery is an essential component of the inhibition of tumor cell telesis (programmed cell growth) and eventual apoptosis (programmed cell death). Cancer treatment with paclitaxel has been coupled with different therapeutic modalities which include radiation and/or chemotherpeutic agents as described earlier. For in vitro studies many different breast cancer cell lines have been utilized to establish the effects of combination of drugs. Nude mouse model with implanted human breast cancer cells have been utilized in a number of studies. In these studies drugs have been delivered in a variety of ways including intraperitoneal, intravenous or subcutaneous injections. The vehicle for drug delivery is also an essential component as it affects drug stability, toxicity and pharmacokinetics. Paclitaxel has been delivered in cremophore or liposomes in many animal studies (33). Sphingolipids have been delivered in vivo via liposome preparations (34).

These preliminary studies with squamous cell carcinoma in nude mice (Balb/c strain, Taconic Farms, N.Y.) paclitaxel and ceramide were delivered in very small amounts in cremophore and alcohol respectively. In the first phase of these studies the paclitaxel is delivered in cremophore and C6-ceramide in alcohol solution diluted with culture medium. These studies include all appropriate vehicle controls (medium, alcohol and/or cremophore alone) in appropriate concentrations. The experimental and control group also includes paclitaxel, ceramide and a combination of paclitaxel and ceramide. These agents are delivered on day 4 after the implantation of MCF-7 (breast cancer cell line) cells in nude mice. Appropriate drugs are injected subcutaneously three times weekly and the growth of tumor is followed for approximately 6-8 weeks. This time period is derived from preliminary studies on head and neck cancer cells in nude mice. These studies are initially done in various groups (including controls all done at the same time) with 5 mice each. This set of studies is repeated at least 3 times and the data subjected to statistical analysis to obtain the confidence limits.

As indicated earlier liposome preparations of paclitaxel have been as efficacious or better than standard preparations in cremophore. Also, liposome preparations of sphingolipids have been shown to have greater effect because of its stability than free sphingolipids (34). Therefore, C6-ceramide may be prepared in liposomes as indicated in the methods section. The experimental design with liposomal formulations includes appropriate controls including lipsome preparations without ceramide and/or paclitaxel. Liposome formulations may be administered intraperitoneally as well.

A set of in vitro experiments is performed to assess the effect of lipsome formulations on MCF-7 with appropriate controls. In these experiments, cells are subjected simultaneously or sequentially with paclitaxel and ceramide. If results indicate simultaneous treatment to be better than sequential treatment then a single liposome formulation with paclitaxel and ceramide combined will be prepared and tested again with its appropriate controls as indicated earlier. A minimum of 15 nude mice in three separate sets of experiments are tested in experimental protocols. Based on studies with squamous carcinoma cells that a sum total of these experiments provide enough samples to be tested for significance by statistical analysis.

For the evaluation of the combined effects of paclitaxel and ceramide in vivo the following measurements are performed: (1) tumor growth in millimeters, (2) excised tumor weight at the completion of experiments, (3) histopathology of excised tumors and (4) the identification of apoptotic cells using TUNEL method. The measurement of tumor growth and weight is a routine procedure and is performed by a trained animal technician. The identification of apoptotic cells by TUNEL assay is also a routine procedure in the laboratory and is performed on a FACScan flow cytometer which is part of the core facility available to all investigators. The histopathology of the excised tumors is then performed.

The evaluation of the combined effects of paclitaxel and ceramide on MCF-7 cells in vitro involve the measurement of cell growth by a tetrazolium (MTT) dye assay (a routine procedure), apoptosis by TUNEL assay and cell cycle progression by flow cytometry (also a routine procedure).

The liposome formulations are prepared by a standard lipid film procedure. Briefly, paclitaxel, cardiolipin, cholesterol and phosphotidylcholine are dissolved in chloroform-methanol mixture as described (33, 34). The solvents are evaporated in a rotary evaporator under vacuum. The hydrated film is dispersed by vigourous mixing. The small unilamellar liposomes are then obtained by sonication. The amount of drug entrapped is determined by standard reverse-phase high pressure liquid chromatography. The stability of these preparations is determined first by regular in vitro cell growth inhibition assays on MCF-7 cells in comparison to paclitaxel in cremophore and ceramide in alcohol solutions. The liposome formulations are utilized based on their stability assays. It is anticipated that these preparations will be stable for a period of 4 weeks at 4° C. The usual problem with the liposome formulations is the fusion of the final product with time. In such situations the formulated products are sized through an extruder using 50 nm NUCLEOPORE membrane.

REFERENCES FOR 5TH SERIES OF EXPERIMENTS

1. Ford, R., A. Goodacre, S. Mehta, and F. Cabanilas. Establishment and characterization of human neoplastic B-cell lines. Blood. 75: 1311, 1990.
2. Mendelsohn, M. The growth fraction: A new concept applied to tumors. Science. 132: 1496, 1960.

3. Devita, V., C. Denham, and S. Perry. Relationship of normal CDF1 mouse leucocyte kinetics to growth characteristics of leukemia L1210. Cancer Res. 29: 1067-1071, 1969.
4. Goldi, J. and A. Coldman. A mathematic model for relting the drug sensitivity of tumors to the spontaneous mutation rate. Cancer Treat. Rep. 63: 1727-1733, 1979.
5. Wani, M., H. Taylor, M. Wall, P. Coggan, and A. McPhail. Plant antitumor agents VI. The isolation and structure of taxol, a a novel antileukemic and antitumor agent from *Taxus brevifolia*. Am. Chem. Soc. 93: 2325-2337, 1971.
6. Owellen, R., C. Hartke, R. Dickinson, and F. Hains. Inhibition of tubulin microtubulin polymerization by drugs of the Vinca alkaloid class. Cancer Res. 36: 1499-1502, 1976.
7. Howitz, S. B., D. Cohen, S. Rao, I. Rignel, H. Shen, and C. H. Yang. Taxol: Mechanisms of Action and Resistance. J. Natl. Cancer Inst. (Monographs). 15: 55-61, 1993.
8. Buzdar, A., F. Holmes, and G. Hortobagyi. Paclitaxel in the treatment of metastatic breast cancer. M.D. Anderson Cancer Center experience in the Emerging Role in Pacitaxel in Cancer Chemotherapy. Sem Oncol. 22(3) Suppl 6: 101-104, 1995.
9. Sledge, G., N. Robert, J. Sparano, M. Cogleigh, L. Goldstein, D. Neuberg, E. Rowinsky, C. Baughman and W. McCaskill-Stevens. Eastern Cooperative Oncology Group Studies of Pacitaxel and Doxorubicin in Advanced Breast Cancer in the Emerging Role of Pacitaxel in Cancer Chemotherapy. Sem Oncol. 22(3) Suppl 6: 105-108, 1995.
10. O'Reilly, S. And K. Gelmon. Biweekly pacitaxel and cis-platinum: A Phase I/II study in the First-Line treatment of metastatic breast cancer in the Emerging Role of Pacitaxel in Cancer Chemotherapy. Sem Oncol. 22(3) Suppl 6: 109-111, 1995.
11. Sessa, C., O. Pagani, G. Parma, A. Goldhirsch, and F. Cavalli. Dose-Finding Study of Paclitaxel and Cyclophosphamide in Patients with Advanced Breast Cancer in the Emergin Role of Pacitaxel in Cancer Chemotherapy. Sem Oncol. 22(3) Suppl 6: 112-117, 1995.
12. Perez, E. A. and C. A. Buckwalter. Sequence-dependent cytotoicity of etoposide and paclitaxel in human breast and lung cancer cell lines. Cancer Chemother. Pharmacol. 41(6): 448-452, 1998.
13. Liebmann, J. E., J. Fisher, D. Teague and J. A. Cook. Sequence dependence of paclitaxel (Taxol) combined with cisplatin or alkylators in human cancer cells. Oncol. Res. 6(1): 25-31, 1994.
14. Kurbacher, C. M., U. Wagner, B. Kolster, P. E. Andreotti, D. Krebs, and H. W. Bruckner. Ascorbic acid (vitamin C) improves the antineoplastic activity of doxorubicin and cisplatin, and paclitaxel in human breast carcinoma cells in vitro. Cancer Lett. June 5, 103(2): 183-189, 1996.
15. Fan, S., B. Chemey, W. Reinhold, K. Rucker, and P. M. O'Connor. Disruption of p53 function in immortalized human cells does not affect survival or apoptosis after taxol or vinicristine treatment. Clin. Cancer Res. Apr. 4(4):1047-1054, 1998.
16. Baselga, J., A. D. Seidman, P. P. Rosen and L. Norton. HER2 overexpression and paclitaxel sensitivity in breast cancer: therapeutic implications. Oncol., March 11 (3 suppl 2), 43, 1997.
17. Nielsen, L. L., P. Lipari, J. Dell, M. Gurnani and G. Hajian. Adenovirus-mediated p53 gene therapy and paclitaxel have synergistic efficacy in models of human head and neck, ovarian, prostate and breast cancer. Clin. Cancer Res., 4, 835-846, 1998.
18. DeNardo, S., L. Kroger, L. Lamborn, L. Miers, R. O'Donnell, D. Kukis, C. Richman and G. DeNardo. Importance of temporal relationships in combined modality radioimmunotherapy of breast carcinoma. Cancer, 80, 2583-2590, 1997.
19. Klaubner, N., S. Parangi, E. Flynn, E. Hammel and R. D'Amato. Inhibition of angiogenesis and breast cancer in mice by the microtubule inhibitors 2-methoxyestradiol and taxol. Cancer Res. 57, 81-86, 1997.
20. Hannun, Y. The sphingomyelin cycle and the second messenger function of ceramide. J Biol Chem 269, 3125, 1994.
21. Bose, R., M. Verheji, A. Haimovits-Friedman, K. Scotto, Z. Fuks, and R. Kolesnick. Ceramide synthase mediates daunorubicin-induced apoptosis: and alternative mechanism for generting death signals. Cell, 82: 405-414, 1995.
22. Strum, J. C., G. W. Small, S. B. Daiug, and L. W. Daniel. 1-B-D arabinofuranosylcytosine stimulates ceramid and diglyceride formation in HL-60 cells. J. Biol. Chem. 269, 15493, 1994.
23. Jayadev, S., B. Liu, A. E. Bielawska, J. Y. Lee, F. Nazaire, M. Pushkareva, L. M. Obeid, and Y. A. Hannun. Role for ceramide in cell cycle arrest. J. Biol. Chem., 270, 2047, 1995.
24. Bielawska, A., C. M. Linardic, and Y. A. Hannun. Modulation of cell growth and differentiation by ceramide. FEBS Lett, 307, 211, 1992.
25. Obeid, L. M. and Y. A. Hannun. Ceramide: a stress signal and mediator of growth suppression and apoptosis. J. Cell Biochem., 58, 191, 1995.
26. Jarvis, W. D., R. N. Kolesnick, F. A. Formari, R. S. Traylor, D. A. Gewirtz, and S. Grant. Induction of apoptotic DNA damage and cell death by activation of the sphingomyelin pathway. Proc. Natl. Acad. Sci. USA 91, 73, 1995.
27. Cai, Z., A. Bettaieb, N. E. Mabdani, L. G. Legres, R. Stancou, J. Masliah, and S. Chouaib. Alteration of the sphingomyelin/cramide pathway is associated with resistance of human breast carcinoma $MCF_7$ cells to tumor necrosis factor-alpha-mediated cytoxicity. J. Biol. Chem., 272(11):6918-6926, 1997.
28. Gill, Z. P., C. M. Perks, P. V. *Newcomb*, and J. M Holly. Insulin-like growth factor-binding protein (IGFBP-3) predisposes breast cancer cells to programmed cell death in a non-IGF-dependent manner. J. Biol. Chem., 272(41): 25602-25607, 1997.
29. Gill, J. S, and A. J. Windebank. Role of ceramide in suramin-induced cancer cell death. Cancer Lett., 119(2): 169-176, 1997.
30. Haldar, S., J. Chintapalli and C. Croce. Taxol induces bcl-2 phosphorylation and death of prostate cancer cells. Cancer Res., 56, 1253, 1996.
31. Amato, S., J. Swart, M. Berg, H. Wanebo, S. Mehta and T. Chiles. Transient stimulation of the c-Jun-$NH_2$-terminal kinase/activator protein 1 pathway and inhibition of extracellular signal-regulated kinases are early effects in paclitaxel-mediated apoptosis in human B lymphoblasts. Cancer Res., 58, 241, 1998.
32. Haimovitz-Friedman, A., R. Kolesnick and Z. Fuks. Ceramide signaling in apoptosis. Br. Med. Bull, 53, 539, 1997.
33. Cabanes, A., K. Briggs, P. Gokhale, J. Treat and A. Rahman. Comparative in vivo studies with paclitaxel and liposome-encapsulated paclitaxel. Intl. J. Oncol., 12, 1035, 1998.
34. Shirabama, T., E. Sweeney, C. Sakakura, A. Singhal, K. Nishiyama, S. Akiyama, S. Hakamori and Y. Igarashi. In vitro and in vivo induction of apoptosis by sphingosine and N,N-dimethylsphingosine in human epidermoid carcinoma KB-3-1 and its multidrug-resistant cells. Clin. Cancer Res, 3, 257-264, 1997.

What is claimed is:

1. A method for inhibiting growth of a tumor comprising head and neck squamous carcinoma cells, which method comprises contacting the tumor with
   (a) an amount of paclitaxel, and
   (b) an amount of $C_6$-ceramide, sequentially or concomitantly, wherein the amount of paclitaxel and the amount of $C_6$-ceramide in combination are effective to induce at least a 50% growth inhibition, thereby inhibiting growth of the tumor, and wherein the ratio of the amount of $C_6$-ceramide relative to the amount of paclitaxel is at least 4.167 to 1.

2. The method of claim 1, wherein the tumor is first contacted with paclitaxel and subsequently contacted with $C_6$-ceramide.

3. The method of claim 1, wherein the tumor is present in a subject.

4. The method of claim 1, wherein the contacting with paclitaxel is effected by cremophore-mediated delivery or liposome-mediated delivery, and the contacting with $C_6$-ceramide is effected by cremophore-mediated delivery, alcohol-mediated delivery or liposome-mediated delivery.

5. The method of claim 3, wherein the contacting with paclitaxel and with $C_6$-ceramide is effected by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

6. A method of decreasing the size of a tumor, comprising tumor cells, wherein the tumor cells are head and neck squamous cell carcinoma cells which method comprises contacting the tumor with
   (a) an amount of paclitaxel, and
   (b) an amount of $C_6$-ceramide, sequentially or concomitantly, wherein the amount of paclitaxel and the amount of $C_6$-ceramide in combination are effective to induce apoptosis of the tumor cells, and wherein the decrease in size of the tumor is greater than the decrease in size caused by contacting the tumor with either paclitaxel alone or $C_6$-ceramide alone, thereby decreasing the size of the tumor, and wherein the ratio of the amount of $C_6$-ceramide relative to the amount of paclitaxel is at least 4.167 to 1.

7. The method of claim 6, wherein the tumor is first contacted with paclitaxel and subsequently contacted with $C_6$-ceramide.

8. The method of claim 6, wherein the tumor is present in a subject.

9. The method of claim 6, wherein the contacting with paclitaxel is effected by cremophore-mediated delivery or liposome-mediated delivery, and the contacting with $C_6$-ceramide is effected by cremophore-mediated delivery, alcohol-mediated delivery or liposome-mediated delivery.

10. The method of claim 8, wherein the contacting with paclitaxel and with $C_6$-ceramide is effected by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

11. A method for treating a subject afflicted with head and neck squamous cell cancer, which method comprises administering to the subject an amount of paclitaxel and an amount of $C_6$-ceramide, sequentially or concomitantly, wherein the amount of paclitaxel and the amount $C_6$-ceramide in combination are effective to induce at least a 50% growth inhibition of the cancer cells, thereby treating the cancer, and wherein the ratio of the amount of $C_6$-ceramide relative to the amount of paclitaxel is at least 4.167 to 1.

12. The method of claim 11, wherein paclitaxel is first administered and $C_6$-ceramide is subsequently administered to the subject.

13. The method of claim 11, wherein $C_6$-ceramide is first administered and paclitaxel is subsequently administered to the subject.

14. A method for inhibiting growth of a tumor comprising pancreatic cancer cells, which method comprises contacting the tumor with
   (a) an amount of paclitaxel, and
   (b) an amount of $C_6$-ceramide, sequentially or concomitantly, wherein the amount of paclitaxel and the amount of $C_6$-ceramide in combination are effective to induce at least a 50% growth inhibition, thereby inhibiting growth of the tumor, and wherein the ratio of the amount of $C_6$-ceramide relative to the amount of paclitaxel is at least 4.167 to 1.

15. The method of claim 14, wherein the tumor is first contacted with paclitaxel and subsequently contacted with $C_6$-ceramide.

16. The method of claim 14, wherein the tumor is present in a subject.

17. The method of claim 14, wherein the contacting with paclitaxel is effected by cremophore-mediated delivery or liposome-mediated delivery, and the contacting with $C_6$-ceramide is effected by cremophore-mediated delivery, alcohol-mediated delivery or liposome-mediated delivery.

18. The method of claim 16, wherein the contacting with paclitaxel and with $C_6$-ceramide is effected by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

19. A method of decreasing the size of a tumor, comprising tumor cells, wherein the tumor cells are pancreatic cancer cells,—which method comprises contacting the tumor with
   (a) an amount of paclitaxel, and
   (b) an amount of $C_6$-ceramide, sequentially or concomitantly, wherein the amount of paclitaxel and the amount of $C_6$-ceramide in combination are effective to induce apoptosis of the tumor cells, and wherein the decrease in size of the tumor is greater than the decrease in size caused by contacting the tumor with either paclitaxel alone or $C_6$-ceramide alone, thereby decreasing the size of the tumor, and wherein the ratio of the amount of $C_6$-ceramide relative to the amount of paclitaxel is at least 4.167 to 1.

20. The method of claim 19, wherein the tumor is first contacted with paclitaxel and subsequently contacted with $C_6$-ceramide.

21. The method of claim 19, wherein the tumor is present in a subject.

22. The method of claim 19, wherein the contacting with paclitaxel is effected by cremophore-mediated delivery or liposome-mediated delivery, and the contacting with $C_6$-ceramide is effected by cremophore-mediated delivery, alcohol-mediated delivery or liposome-mediated delivery.

23. The method of claim 21, wherein the contacting with paclitaxel and with $C_6$-ceramide is effected by an administration route selected from the group consisting of intravenous, intraperitoneal, intrathecal, intralymphatic, intramuscular, intralesional, parenteral, epidural, subcutaneous, pleural, topical, oral, nasal, anal, ocular and otic.

24. A method for treating a subject afflicted with pancreatic cancer, which method comprises administering to the subject an amount of paclitaxel and an amount of $C_6$-ceramide, sequentially or concomitantly, wherein the amount of paclitaxel and the amount $C_6$-ceramide in combination are effective to induce at least a 50% growth inhibition of the cancer cells, thereby treating the cancer, and wherein the ratio of the amount of $C_6$-ceramide relative to the amount of paclitaxel is at least 4.167 to 1.

25. The method of claim 24, wherein paclitaxel is first administered and $C_6$-ceramide is subsequently administered to the subject.

26. The method of claim 24, wherein $C_6$-ceramide is first administered and paclitaxel is subsequently administered to the subject.

* * * * *